United States Patent
Singh

(10) Patent No.: US 10,081,376 B2
(45) Date of Patent: Sep. 25, 2018

(54) RAIL TRACK ASSET SURVEY SYSTEM

(71) Applicant: Sameer Singh, Castle Donington (GB)

(72) Inventor: Sameer Singh, Castle Donington (GB)

( * ) Notice: Subject to any disclaimer, the term of this patent is extended or adjusted under 35 U.S.C. 154(b) by 244 days.

(21) Appl. No.: 14/982,212

(22) Filed: Dec. 29, 2015

(65) Prior Publication Data

US 2017/0066459 A1  Mar. 9, 2017

(30) Foreign Application Priority Data

Sep. 3, 2015 (GB) .................................. 1515648.2

(51) Int. Cl.
*G06K 9/00* (2006.01)
*B61L 23/04* (2006.01)
(Continued)

(52) U.S. Cl.
CPC .............. *B61L 23/042* (2013.01); *B61K 9/08* (2013.01); *B61L 15/0072* (2013.01); *B61L 15/0081* (2013.01); *B61L 23/04* (2013.01); *B61L 23/044* (2013.01); *B61L 23/045* (2013.01); *B61L 23/047* (2013.01); *B61L 23/048* (2013.01); *B61L 25/021* (2013.01); *B61L 25/023* (2013.01); *B61L 25/025* (2013.01); *G01B 11/22* (2013.01); *G01N 21/8851* (2013.01); *G06K 9/00771* (2013.01); *G06K 9/46* (2013.01); *G06K 9/6202* (2013.01); *G06K 9/628* (2013.01); *G06K 9/6215* (2013.01); *G06K 9/6218* (2013.01); *H04N 5/247* (2013.01); *B61L 2205/04* (2013.01);
(Continued)

(58) Field of Classification Search
USPC ......................................................... 382/106
See application file for complete search history.

(56) References Cited

U.S. PATENT DOCUMENTS 7,706,573 B1 * 4/2010 Motamedi ................ G01C 1/00
                                                         382/106
9,049,433 B1   6/2015 Prince
(Continued)

FOREIGN PATENT DOCUMENTS

EP          1236634 A1      9/2002

OTHER PUBLICATIONS

European Search Report in corresponding European Application No. 16 18 5039, dated Jan. 18, 2017, 2 pages.
(Continued)

*Primary Examiner* — Alex Liew
(74) *Attorney, Agent, or Firm* — Law Office of Jeff Williams; J. Oliver Williams

(57) ABSTRACT

The present application involves a railroad track asset surveying system comprising an image capture sensor, a location determining system, and an image processor. The image capture sensor is mounted to a railroad vehicle. The location determining system holds images captured by the image capture sensor. The image processor includes an asset classifier and an asset status analyzer. The asset classifier detects an asset in one or more captured images and classifies the detected asset by assigning an asset type to the detected asset from a predetermined list of asset types according to one or more features in the captured image. The asset status analyzer identifies an asset status characteristic and compares the identified status characteristic to a predetermined asset characteristic so as to evaluate a deviation therefrom.

47 Claims, 14 Drawing Sheets

(51) Int. Cl.
  *B61K 9/08*    (2006.01)
  *B61L 15/00*   (2006.01)
  *G06K 9/46*    (2006.01)
  *G06K 9/62*    (2006.01)
  *H04N 5/247*   (2006.01)
  *B61L 25/02*   (2006.01)
  *G01B 11/22*   (2006.01)
  *G01N 21/88*   (2006.01)

(52) U.S. Cl.
  CPC ..... *G01N 2201/10* (2013.01); *G01N 2201/12* (2013.01); *G06K 2209/19* (2013.01)

(56) References Cited

U.S. PATENT DOCUMENTS

| | | | |
|---|---|---|---|
| 2002/0041698 A1* | 4/2002 | Ito | G06T 7/254 382/103 |
| 2007/0291994 A1* | 12/2007 | Kelle | G01C 11/00 382/110 |
| 2011/0064273 A1 | 3/2011 | Zarembski et al. | |
| 2012/0192756 A1 | 8/2012 | Miller et al. | |
| 2012/0263342 A1 | 10/2012 | Haas et al. | |
| 2012/0274772 A1 | 11/2012 | Fosburgh | |
| 2013/0096739 A1 | 4/2013 | Landes et al. | |
| 2013/0191070 A1 | 7/2013 | Kainer | |
| 2013/0230212 A1* | 9/2013 | Landes | G06K 9/00791 382/104 |
| 2013/0261950 A1* | 10/2013 | Sasabuchi | B61L 23/041 701/301 |
| 2015/0201165 A1 | 7/2015 | Bocionek | |

OTHER PUBLICATIONS

United Kingdom Intellectual Property Office Search Report in corresponding UK application No. GB1515648.2, dated Feb. 11, 2016, 4 pages.

\* cited by examiner

RAIL TRACK ASSET SURVEY SYSTEM

BACKGROUND

1. Field of the Invention

The present invention relates to the surveying of rail track assets, such as objects or equipment in the vicinity of a railroad.

2. Description of Related Art

Assets in the vicinity of rail tracks are important for signalling and running of trains on the track. These include assets related to signalling, trackside monitoring, driver assistance and instruction, and track components.

Conventionally, in managing rail track assets, a list of well-known assets is maintained, including locations of said assets. These typically include information on important assets such as signals, but may not include information on smaller or less significant assets. The list of assets is generally maintained manually, at high cost. This is highly time consuming, and the list quickly becomes out of date.

Previously, track surveys were carried out by a team of inspectors who would walk along the track or travel on slow speed motorised platforms, making records of track components and their condition and location. This process of data capture was very slow, as the speed to travel needed to be sufficiently slow in order that the track inspectors could record data. Any interruption to normal use of the track for higher speed passenger and freight vehicles is detrimental. If inspectors travel on conventional passenger trains, then it is necessary to conduct multiple passes of the same stretches of the track to accurately identify all rail track assets of potential concern.

More recently, digital cameras have been used on board an inspection vehicle, to record video of the track and its surroundings, and to log location data. Typically, image data is transferred to an off-site computer, where a human operator, with the assistance of desktop software, reviews the collected data and manually selects assets of interest from the images. This is typically a slow and expensive process; it may take several weeks or months to complete a survey of a moderately sized track segment, in which time the conditions of the assets may have changed significantly.

There have been more recent attempts to use video image frame processing techniques to identify assets against predetermined templates for a small number of asset types. Whilst such techniques can potentially identify and classify different types of asset, this does not result in a complete surveying system in itself because the operational risk posed by the identified assets is not inferred by the asset type alone. Manual inspection/assessment would rely on the inspector to drawn upon a significant level of underlying knowledge about the different types of assets and the risks that could be posed to railway track and/or rail vehicles thereby. Thus, even though the process of capturing image data for a survey has been simplified and made accessible to an inspector, the risk assessment itself remains a substantially manual process and the time taken to complete a survey thus increases generally linearly as a function of the length of track to be inspected.

One particular complexity of an asset inspection system for use in rail applications is that video image processing can be computationally intensive. The requirement for data to be amassed and communicated to a central location for processing, coupled with the detailed processing of the recorded data, can lead to a significant delay between the inspection itself and the deduction of any action required based on the inspection. Furthermore it can be problematic handling the large volumes of image/video data generated.

It is an object of the present invention to provide a track asset surveying system that overcomes or substantially mitigates one or more of the above disadvantages associated with conventional track asset surveying. It may be considered an additional or alternative aim of the invention to provide a system that can provide useful inspection results closer to in real time.

Although great strides have been made, considerable shortcomings remain.

SUMMARY OF THE INVENTION

According to an aspect of the invention there is provided a railroad track asset surveying system comprising an image capture sensor mounted on a railroad vehicle, a location determining system for images captured by the sensor and an image processor, the image processor comprising an asset classifier for automatic detecting an asset in one or more captured image and classifying the detected asset by assigning an asset type to the detected asset from a predetermined list of asset types according to one or more feature in the captured image, and an asset status analyser for automatically identifying an asset status characteristic and comparing the identified status characteristic to a predetermined asset characteristic so as to evaluate a deviation therefrom.

The image sensors used for track inspection as a part of this invention may generate images using a range of cameras, or numerical measurement data as with lasers which can provide a two or three dimensional view of the scene.

The image capture sensor may comprise a shape and/or surface property sensor. The image capture sensor may comprise a brightness and/or colour/texture sensor, e.g. for detecting one or more surface property of an asset. The image capture sensor may comprise a light sensor, e.g. for capturing a visual image, such as a camera. Additionally or alternatively, the image capture sensor may comprise either or both of a laser or thermal image capture sensor.

A laser measurement sensor may comprise an image capture sensor and/or a distance measurer. One or more laser sensor may record a three dimensional profile of a surface on which a laser beam is projected. A spinning laser may be employed. A three dimensional point cloud data set may be generated to represent one or more asset or the scene.

One or more shape/geometric feature of the asset, such as an edge or dimension, may be determined from a surface property sensor or the laser measurement sensor.

A plurality of image capture and/or laser measurement sensors may be used, such as a plurality of the same or different types of sensors. Different sensor types may comprise sensors for different electromagnetic radiation types/wavelengths. Alternatively different image sensor types may comprise different sensor dimensionality or orientation, e.g. such as area scan, line scan, depth detection sensors and/or three-dimensional imaging devices, such as laser scanners. Automatic asset classification and or status assessment may be beneficially improved by one or multiple asset view analysis.

One or more image sensor or other sensor type may be used for asset depth/distance detection.

The different sensor types may be used in parallel. For example, the output of each sensor may be used to assess assets independently, e.g. using the same or a different type of assessment depending on sensor type. The asset classifier and/or asset status analyser may receive the different sensor inputs and may use them in combination to determine an asset classification and/or asset status. The combination of different modalities in this manner can provide greater certainty of automated asset surveying, for example in which a finding using one modality is compared to a corresponding finding using another modality in order to confirm or reject that finding.

One or more image capture sensor may be used for rail track imaging, e.g. whilst one or more further image capture sensor may be used for assessing other assets in the vicinity of the railroad track. Different types or orientations of image capture and/or laser measurement sensor may be used for those different purposes. A laser scanner may be used for scanning the track/track bed and/or the environment in the vicinity of the track.

One or more image capture sensor may be forward facing in the direction of travel of the vehicle. A plurality of image capture sensors may be forward facing, which may have an at least partially overlapping field of view. One or more image capture sensor may be downward facing, e.g. towards the track passing beneath the vehicle, and/or upward facing, e.g. facing overhead wires. With reference to the axis of travel of the vehicle, any image capture sensor may be parallel, obliquely angled and/or perpendicular, e.g. according to its intended purpose.

Images captured by a plurality of image capture sensors, and/or images captured by the same sensor in time sequence, may be concatenated by the processor, e.g. to form a resulting image comprising said plurality of concatenated images. This may be useful in capturing the whole of an asset in a single image or else in ensuring continuity of imaging. Captured images may be concatenated to provide a single image showing the entire width of the track, e.g. from one sleeper end to another, and potentially to include a surrounding region beyond the sleeper ends.

The image capture sensor(s) may be adjustably mounted to the vehicle, e.g. to adjust the field of view of the image capture sensor(s). Angular adjustment may be used. Adjustment of a lens and/or aperture may be used to adjust (e.g. widen/reduce) the sensor field of view.

The asset status analyser is advantageous in that it can contribute to identification of an operational risk associated with the asset, such as degradation of the asset and/or a potential impact of the asset on current or future operation of a railroad vehicle on the railroad track. The predetermined asset status characteristic may comprise one or more of a nominal or normal asset status characteristic, a threshold asset status characteristic for a normal/abnormal status and/or a previously determined asset status characteristic for the same asset or asset type.

The use of an asset classifier and asset status analyser may be part of an automated railroad track asset surveying system that does not demand manual inspection and/or manual interpretation of asset images as part of the survey process. The steps from image or laser data acquisition to its processing, recording of results, and reporting may be fully automated. The asset status analyser may output an indication of asset condition or health.

A phase shift modulation and/or triangulation approach to laser measurements may be used for asset surveying, e.g. for asset classification and/or status determination.

Imaging of the railroad track may be used to assess an orientation, or rate of change in orientation, of the track, such as track curvature. The track may be treated as an asset and may be classified according to predetermined track features. A longitudinal axis for the track may be determined and the curvature of said longitudinal axis may be output at a plurality of locations along the track. Track tilt may be determined according to an angular orientation of the track in a lateral direction relative to the longitudinal axis.

The orientation/curvature of the track at a location that corresponds to the location of an asset may provide an input to the asset status analyser and/or may affect the asset status characteristic. Track orientation may be sensed either by the imaging sensor(s) and/or a further orientation sensor, such as a compass or inclinometer. Any of track curvature, tilt or inclination may alter an acceptance threshold for an asset status characteristic.

The system may comprise a vibration sensor. Vibration may be sensed as an indication of track status and may be logged by the system, e.g. with a location record. Vibration input may provide one of a plurality of inputs used in asset status analysis.

The images/assets captured by the one or more sensor may be logged with a location record (e.g. a geographical location record) from the location determination system. The location record may correspond to the sensor location, e.g. including a determined asset spacing therefrom. Where a plurality of sensors are used the corresponding images and/or laser data captured by the plurality of sensors may be logged with a common location record. In any examples, the location record may be supplemented or substituted for a time record (e.g. a timestamp). Location indexing may be performed, e.g. by one or more software module of the image processor, which may take location and time-stamp data from a location record, e.g. from one or more location sensor, and indexes image sensor and/or other sensor data with it. A record of raw sensor data entries (images, or flat file values) may be maintained. Any or any combination of said image data and location record data may be stored in a common data store for the system, which may comprise one or more database.

The location record may comprise a plurality of components (e.g. latitude and longitude) according to a geographic coordinate system. The location record may additionally or alternatively comprise a local or relative coordinate value, e.g. relative to the railroad track. The location record may comprise a one-dimensional location record component or value, e.g. according to distance along the railroad from a datum point.

The position of an asset may be referenced by its distance from track centreline and longitudinal distance along the track from a fixed point of reference. A range of asset features or properties can be stored for the detected asset including its unique identifier, size, dimensions, centre point, colour and texture characteristics, topological data, condition data, and so on. The spacing may be a perpendicular spacing, e.g. comprising a lateral and/or vertical spacing/component, from an axis or vertical plane associated with the track. A clearance from the track or an overhead cable may be logged.

The location determination system may comprise a vehicle travel distance sensor, such as a tachometer, and/or a track position sensor. This may be used in addition to, or instead of, a GPS location system. Combining multiple location determination systems/sensor types may be used to increase the accuracy of asset location determination. A track position sensor may comprise a sensor for identifying track features indicative of known/predetermined track locations, e.g. fixed datum locations. An imaging sensor could be used for this purpose or else a near-field wireless communication transmitter receiver. An RFID scanner mounted on the train, for example, could be used to detect RFID tags mounted on the track at known locations. A lookup table of known tag locations may be used to determine asset and/or image sensor location.

The rate of image capture may be controlled according to the railroad vehicle travel speed. A predetermined rate of image capture or volume of image data per unit distance may be set. For example, a rate of pixel capture per mm distance along the track could be set. A pulsed signal at a pulse frequency according to vehicle speed could be used to control image/frame capture frequency or scanning rate.

An edge profile/silhouette for each asset may be identified from the captured images. The profile may be compared to a database of predetermined asset features to identify a match for asset classification. Additionally or alternatively, surface texture/colour for each asset may be identified from the captured images. The surface texture/colour may be compared to the database of predetermined asset features to identify a match, or applied to a rule based asset detector/classifier.

Dimension and/or shape measurement of assets may be matched to predetermined shape profiles. One, two or three dimensional shape model constructs and/or analysis may be used. For example some assets, such as signage, may be best matched using a two-dimensional model, whereas other assets may be best matched using a three-dimensional model/analysis. For three-dimensional analysis, point cloud data (e.g. scan data) may be collated in a single or a plurality of passes of the asset. In addition to a matching approach, a rule based approach to asset detection and classifier may also be employed using dimension and shape measurements.

Asset template matching may be used according to geometric asset templates, which may comprise curvature, edge and/or dimension features. The templates may comprise one or more geometric feature and one or more surface property feature.

A confidence score may be determined for, and/or assigned to, an asset classified by the system according to a degree of the match between the geometric profile and/or surface property (colour/texture) of an asset identified in the captured images and the predetermined asset features. It has been found that the combination of shape matching and colour/texture matching yields significantly certainty in asset identification and condition analysis.

The asset status characteristic may comprise a visibility characteristic. This has been found to be beneficial in providing a risk assessment for trackside assets, such as, for example, signals. The system may log a visibility characteristic according to the degree of the match determined for the geometric profile and/or surface property of an asset. The system can determine the change in visibility characteristic with distance from the asset and thereby determine the distance at which the asset is clearly visible. The system may log a visibility distance for the, or each, asset. Once an asset has been characterised in an image, the system may review a sequence of captured images containing the asset in a forward or reverse order to determine the visibility distance. The visibility distance output may be used for determining driver risk assessment, for example, when approaching signals and level crossings.

The data processing tasks can be performed using an image (visual, laser and/or thermal) data processor. In some instances, a single data processor would be sufficient to do this. The image processor may comprise a plurality of processors/chips, wherein at least one processor is arranged to log captured images and associated location data in real time in a data store, e.g. aboard the vehicle. Said processor may be arranged to collate image and/or associated data from a plurality of sensors/sources. At least one processor may be arranged to process the captured images to identify and/or classify assets substantially in real-time or with a slight time delay, e.g. near-real time. At least one processor may be arranged to perform analytics on the captured images. Raw image data may be logged in parallel with analytical processing. A central controller may determine which of the processes to be carried out concurrently according to data input rate and processing rate.

Image logging may comprise storing digital images/frames as a flat (e.g. binary) pixel data format, or as compressed images with well known formats such as JPEG, e.g. with a location identifier. Similarly, raw data from laser sensors can be logged in a compressed format. For flat file format, image file header information may be added at a subsequent processing stage (e.g. not in real-time or near real-time).

At least one processor may be arranged to process the captured images and/or laser data so as to analyse asset status. The asset surveying system may output asset identification, location and/or status in real-time, e.g. such that there is substantially no delay or negligible delay between when the assets are visible within the sensor field of view, and their detection by the automated asset analyser system. This allows for the operator to view track asset data as the vehicle approaches or passes those assets in real-time. The asset status analyser may output asset status in real time or with a relatively short time delay after image and laser data capture, e.g. in near real-time. In any example of the invention the captured data processing time may comprise a relatively shorter time period or speed compared to the travel time or speed of the vehicle, such as for example a fraction of the travel time/speed, e.g. less than a half or quarter of the vehicle travel time/speed, or an order of magnitude or more less than the vehicle travel time/speed, at normal vehicle speeds. In case of near real-time, there is a short delay between when the sensors are able to view and asset, and when it is registered as found with its measured properties within a database used by asset status analyser. This delay can be variable based on the hardware capability and complexity of data analysis software. The system also allows for off-line data analysis whereby the data is acquired in real-time, but processed off-line at a later time.

The data store may comprise a processed image data store and/or a buffer. The processed image data store may comprise the images, raw laser readings, and associated asset classification and/or status data. The processed image store may comprise location data corresponding to the stored images.

The data processor may comprise a central processor and either or both of a field programmable gate array, e.g. for logging received image/frame data from the image capture sensor(s), and a graphics card. The ability to divide up the processing steps between different processors is beneficial in defining a hierarchy of processing stages, for example such that some processing stages can take precedence and be performed in real time, whilst other most computationally expensive processing can be carried out in near real-time or with a time delay after image capture.

The data processor may comprise a sensor data collation/management module and data analysis module. A more detailed data review module may be provided as part of the system but may be only selectively employed by a central processor.

The asset status analyser may determine the distance/spacing between an asset and the track/rails. The spacing between the asset and track may comprise the, or one, status characteristic. A predetermined threshold minimum distance may be set, e.g. such that an alert can be generated if an asset has encroached on the railroad.

An asset status severity scale may be defined, e.g. indicative of an operational risk posed by the asset. An asset status characteristic may correlate to as point or value on the severity scale. An aggregate of a plurality of asset status characteristics may be determined and output as a point or value on the asset status severity scale. One or more threshold value on the severity scale may be used to determine if an action in relation to an asset is required, such as asset inspection, repair, modification or removal/replacement. A suitable alert may be output in the event that one or more threshold is met/exceeded.

The asset classifier may serve as a novelty/anomaly detector. In the event that the asset classifier identifies a detected asset that does not meet criteria for assigning a predetermined asset type, the asset classifier may log an instance of novel asset detection. The asset classifier may log any or any combination of: images in which the unclassified asset is identifiable; a location of the unclassified asset; processed image data (such as surface property and/or profile) data for the unclassified asset. This log may be later analysed to create a new asset type or assign an existing asset type to the asset.

An alert module may be provided, which may receive the asset status characteristics and determine whether one or more alert condition is met. Alert criteria may be set based on asset type and/or novelty/anomaly detection. Semantic knowledge comparison may be performed prior to alert output, e.g. to avoid false positives, for at least some asset types.

The data processor may be accompanied by additional hardware responsible for image or laser data compression. In some cases, the sensor modules may have a built-in module for data compression or performing a limited set of analytics.

The asset status analyser may perform asset change analysis. The predetermined asset status may comprise a previously determined asset status characteristic, e.g. a geometric or surface characteristic. Changes in asset orientation, shape, edge and/or colour may be monitored. The asset status analyser may compare a current status characteristic with one or more previously determined status characteristic. The system may thus log changes/deterioration of assets, both instantaneously (i.e. between two successive passes of the asset) and also over extended periods of time, such as days, weeks, months, years. Depending on data storage capability, one or more status characteristics may be logged for comparison with later determined status characteristics. Comparison of simple asset status characteristic values may avoid the need to re-process previously logged image data. Previously logged asset status characteristics may be stored in an on board data store, for comparison in real-time or near real-time.

The invention is well suited to matching not only man-made assets but also vegetation analysis. Texture/colour analysis, combined with change analysis is particularly beneficial in assessing the risk posed by vegetation. Specific modules for vegetation status analysis may be provided to assess growth, seasonal change, etc. In certain embodiments, identification of specific vegetation types and/or attributes has been found to be beneficial, e.g. for identification of leaves on railtrack and/or proximity of vegetation to overhead lines or the like.

The image processor may identify pixel clusters within an image according to one or more pixel property, such as brightness or colour. Pixel clusters may be used to determine edge, colour, texture, shape and/or other statistical properties for an asset. A pixel cluster may represent an object, such as an asset or part thereof.

The system may comprise a plurality of asset classifiers, e.g. different types of asset classifier. One asset classifier may or may not comprise a rule-based classifier, e.g. employing statistical and/or semantic rules for asset matching. One asset classifier may or may not comprise a template classifier, e.g. matching an asset shape/surface property using one or more correlation-based matching method, such as a neural network or genetic algorithm. One asset classifier may or may not comprise a feature matching tool, e.g. by which pixel clusters are statistically matched to asset attributes/features in predetermined asset recognition tables.

According to a further aspect of the invention there is provided a railroad track asset surveying method corresponding to the system of the first aspect.

According to a further aspect of the invention there is provided a data carrier comprising machine readable code of the operation of an image processor in accordance with the system or method of the above aspects.

Any of the optional features defined above in relation to the first aspect of the invention may be applied to any further aspect.

The system and method of the invention can generate two and/or three dimensional maps of the track, e.g. in which the assets locations are identified on a map including the track itself.

The invention describes a highly integrated assembly of sensors and asset status analyser hardware within a singular enclosure that removes the need for separating in-cabin (data processing and storage hardware) and out-cabin components (camera and laser sensors). The described system requires minimal external interfaces to power and trigger, and provides a low power, low weight, compact and portable unit which is easy to install and use. Such a design is ideally suited for use on passenger trains. Depending on the choice of sensors and asset status analyser hardware, the system can operate from low vehicle speeds of 1-5 miles per hour up to speeds of high speed trains, e.g. 220 miles per hour.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

Figure 1:
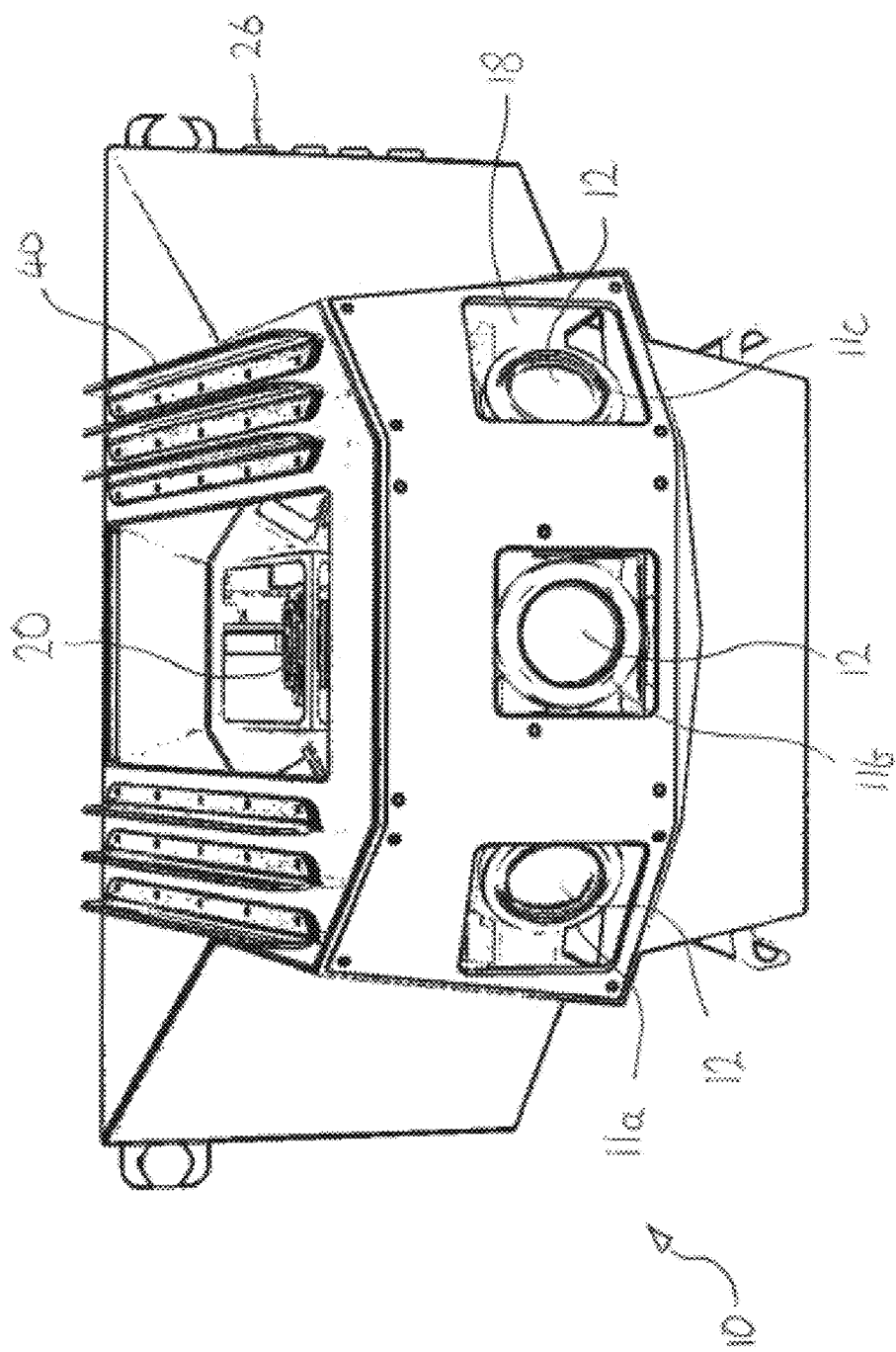
FIG. 1 shows a front view of a housed asset inspection system for mounting to a train.

While the system and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Railroad track, also known as a permanent way, typically consists of rails, fasteners, sleepers (ties), ballast and the underlying subgrade. A number of assets on, or adjacent, the track are important for signalling and running of trains on the track. These include assets related to civil engineering, electrification, signalling, trackside monitoring, driver assistance and instruction, and track components themselves.

FIGS. 1-4 show an example of a housed system 10 for surveying railroad assets, herein termed a "TrackVue". The examples described below concern a single unit or module in which is housed all the equipment required for operation of the asset surveying system. A singular housed unit of this kind is well suited for retrofitting on existing passenger or freight trains and represents an embodiment of the invention that is in many way preferred for ease of installation and operation. However other examples of the invention could comprise a plurality of components or modules mounted at spaced locations on a railroad vehicle but in signal communication via suitable local network connections.

The system 10 includes a plurality of imaging sensors 11, which in this example comprise front facing areascan and thermal imaging sensors 11a, 11b and 11c. Both visible and thermal radiation wavelengths may be sensed at once by a common sensor and subsequently filtered to separate the visible and thermal/infrared images. Alternatively, different individual sensors may be mounted in each imaging unit 11a, 11b and 11c with physical filters to control the wavelengths of radiation detected by each sensor. In either example, separate thermal/infrared (IR) and visible light images can be recorded. In other examples, it is possible to additionally or alternatively use near-IR sensors/filters.

The number and configuration of imaging sensors placed can be varied to cover the entire scene as required. The key properties of each imaging sensor comprise any or any combination of: whether it is color or monochrome; horizontal and vertical image resolution; scanning frequency in hertz; the type of interface with image acquisition devices including GIGE, CAMLINK, USB, etc.; sensor type and size; and, any inbuilt intelligence to perform analysis, data compression or dynamic adjustment of its imaging parameters to cater to changes in the environment. Each forward-facing imaging unit typically has a conventional lens 12.

TrackVue 10 is capable of accommodating a wide variety of imaging sensors, including linescan 14, areascan/thermal 11, and/or laser imaging 16 along with any associated lenses and filters for obtaining the best quality imagery for a desired application. The sensors can be chosen to suit the environment for imaging on a mainline passenger, freight, metro, underground or dedicated inspection train, as well as on rail-adapted vehicles (e.g. hy-rail) and trolley-based platforms such that their imaging sensors can cover the overall area of survey and inspection as desired for a particular application. The lenses 12 can be of fixed or variable focal length and define the field of view required for image capture. Appropriate cut-off filters can be placed to only image within a specific wavelength range, and to reduce the external light interference from certain wavelengths.

Whilst the examples described herein comprise a full complement of imaging sensors, it is intended in examples of the invention, that individual sensors or sensor types will be selectively operable, such that not all sensors are required to be operable at all times. One or more sensor may be triggered for operation at only selected times, or for only certain types of asset inspection, whilst one or more other sensor may be always used.

Each imaging sensor may be placed behind a glass window 18 which protects the sensor from the outside environment.

Figure 2:
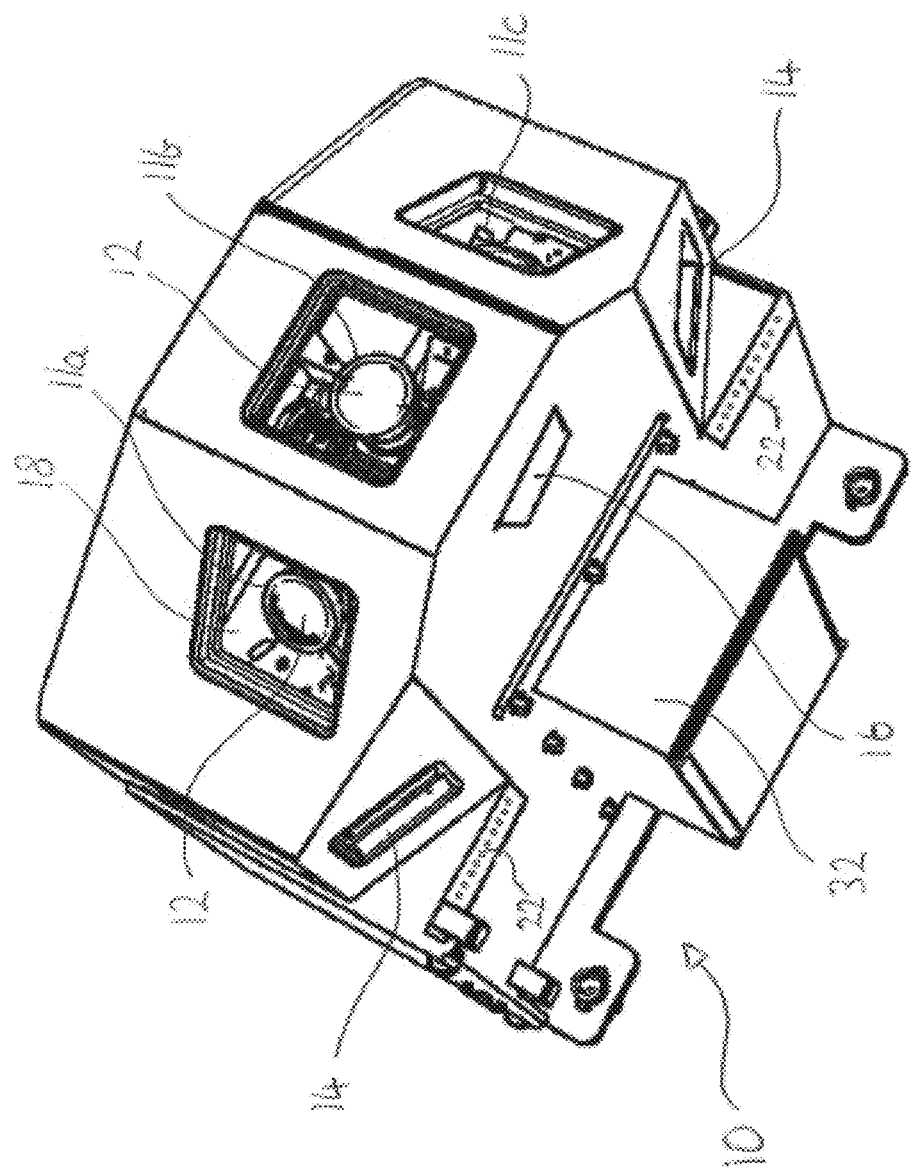
FIG. 2 shows a three-dimensional view of the housed asset inspection system of FIG. 1 from below.

FIGS. 1 and 2 show one example configuration which consists of a centre mounted front facing areascan imaging sensor 11b (e.g. camera) with a wide angled lens 12 and filter to block out excessive sunlight from contaminating the image as well as thermal imaging sensor that can recognise assets that generate a heat signature. The field of view of imaging sensor 11b includes the track in front of the train.

The example of FIGS. 1-4 also shows two side imaging sensors 11a and 11c which are oriented at an angular offset from the axis or orientation of sensor 11b. The angular offset is substantially in a horizontal plane but may include vertical angle offset/adjustment also in other examples. The angular offset of the sensors 11a and 11c in the horizontal plane may be roughly 45° off the axis of alignment of sensor 11b. Sensors 11a and 11c may provide flanking sensors, e.g. for imaging assets to the side of the track in use.

FIG. 1 further shows an overhead areascan and/or thermal imaging sensor 20 which is capable of imaging overhead assets including a view of catenary wires.

FIG. 2 also shows linescan sensors 14 which are positioned to image the rail and surrounding area (i.e. the ground and low lying assets) from a top down view.

For each of the area scan imaging sensors 11a, 11b and 11c and 20, their fields of view can be modified by changing the lens position. A narrower field of view will yield an image where each asset is represented at a higher pixel resolution, whereas the opposite is true for a wider angled lens. The recoded image is a digital representation of the light reflected from various objects in the scene and sensed by the imaging sensor. For a thermal imaging sensor, which may comprise a suitable thermal camera or a thermopile array, a digital image representing the heat sensed is recorded. The temperature values recorded are translated into an image representation that depicts the change in temperature across the scene, e.g. which could be output on a visual display to a human user, and is suitable for automated image analytics. The output of each of thermal and visible light sensors is therefore a sequence of images/frames, each comprising an ordered array of pixels covering the area of interest, each pixel having an associated color, brightness and/or heat energy (temperature) value.

The system allows for adjustment the imaging sensor operation parameters, e.g. dynamically or through applied software control, such as aperture, exposure and gain settings in response to the amount of light detected by its internal sensor, thereby allowing for the recording of better quality images to compensate for any illumination changes over the imaged area.

FIG. 2 shows further details of the imaging sensors mounted in the TrackVue 10 housing which are responsible for downward facing track imaging. By way of an example of one possible configuration, the system of FIG. 2 uses two linescan imaging sensors 14 to image the track in the vicinity of, and including, left and right rails of the track. The cameras 14 are typically angled to view the top of the rail and a rail side along with a region of the ground surrounding it. The area covered depends on the selected lens and can be limited or expanded on the basis of which assets are to be imaged and their distance from rail. A linescan imaging sensor 14 can be color or monochrome (grayscale).

The linescan sensor captures a line on the track at a desired resolution, e.g. by default 0.5 mm, and builds up an image by concatenating the lines together into an image.

The entire track image data can be constructed as a single image from the linescan output. However it is typical to divide the aggregated image data into smaller images, e.g. with the size of each division being decided based on a predetermined number of line scans, distance covered and/or image file size. In this example, a line scan count is maintained and a single image is defined every 2048 or 4096 line scans. The width of the image in pixels is determined by the imaging sensor capability and may be in excess of 1000 pixels, such as typically 2048 pixels or 4096 pixels, although different resolutions may be used for different requirements.

The imaging resolution in pixel per millimeter in the direction of travel is a pre-set value, for example 0.5 mm per pixel, which may be user specified/altered as required. For an imaging sensor to achieve this, it must be fast enough to accommodate the relevant train speed. The imaging resolution in the direction perpendicular to the direction of travel is based on the lens field of view. For example, if an image width is 1000 mm and 2048 pixels represent it, it equates to 0.48 pixels/mm.

The down facing imagery can be undertaken in natural light or with the aid of a light source 22 integrated within or adjacent to TrackVue 10. The light source 22 illuminates the track area imaged by linescan sensors and allows for the capture of potentially better quality images further improving the quality of asset recognition. The light source may comprise an LED light source, e.g. including high powered LED's, operating across either visible or a specific wavelength band so as to ease the asset detection process with automated image analytics on the captured images. The LED light source 22 may comprise of a single or multiple units which can be pulsed as an option to minimise power consumption and keeping the lights cooler.

For forward facing imaging sensors, natural light will predominantly be used, although there exists the option of using a railway vehicle's own headlamp(s) or a bespoke light source as an illumination source if ambient light is insufficient. Additional light sources can be integrated to improve forward facing illumination especially in tunnels and poorly lit areas.

The example system shown in FIG. 2 also incorporates a further imaging system in the form of a laser device 16, which may also be integrated within TrackVue 10. The laser imaging device 16 is capable of profiling the track surface and associated surveyed assets.

The laser device 16 may comprise a conventional laser scanning system that emits laser signals and senses the received reflected signals to determine the location of a reflecting surface in the scanned region. The laser device 16 generates a series of profiles of the track as three dimensional data, typically in the form of point cloud data comprising the locations of points found on the surfaces existing in the scanned region. The scan can have up to 3500 points or more per profile, and the unit can scan at speeds up to 5000 Hz. The frequency of scanning can be chosen based on vehicle speed and desired separation between scans on the track. Each profile covering the breadth of the track and beyond consists of multiple measurements of surface depth. The length, width and orientation of the scan beam can be modified to suit specific applications.

A spinning laser module can be integrated to generate point cloud data for analysis. A spinning laser allows for 360° scan of the environment. Multiple three dimensional laser scan information can be concatenated over time to generate point cloud data showing a complete three dimensional representation of the track.

Also, each pass of a laser device over an asset will generate a different set of point data and so multiple passes/scans of an asset can be accumulated to define a fuller picture of the surfaces being surveyed.

The output of the laser device 16 provides images in the form of geometric data for assets that can be used to determine the profile or shape of each asset.

The system is designed such that the laser light source does not contaminate the readings taken by the other sensors and thus does not interfere with areascan, linescan and/or thermal imaging.

Figure 5:
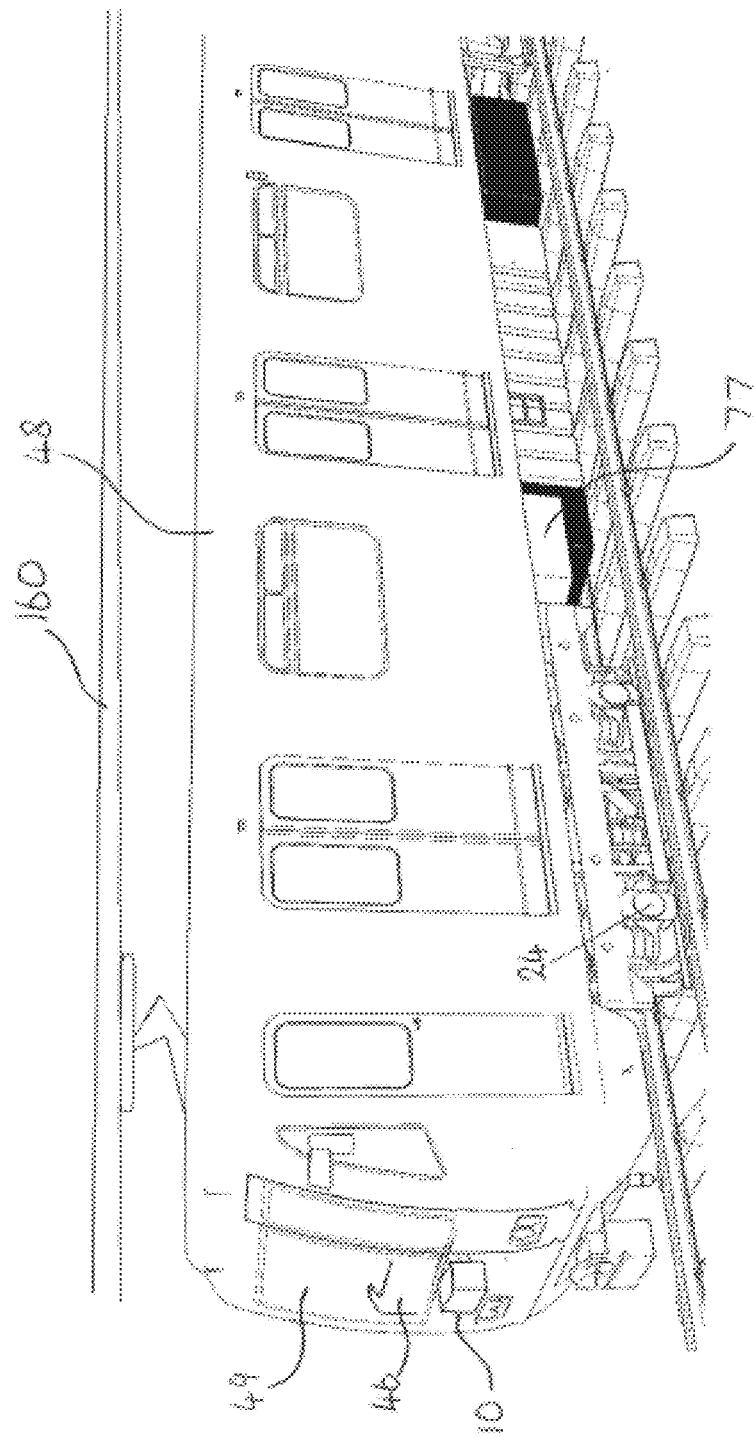
FIG. 5 shows an example of an asset inspection system according to the invention mounted to a train.

For any, any combination or all of the above sensor types, the frequency of image (line, area or volume) capture may be controlled so as to be constant with respect to the distance travelled along the railroad. Thus the frequency or resolution over a length of track may be fixed. In order to achieve this, the frequency of image capture or scanning is controlled based on the vehicle speed. In the present examples, this is achieved by use of a vehicle wheel tachometer 24, e.g. as shown in FIG. 5, to provide a data capture regulation input, although in other examples a similar control scheme could be implemented using any other conventional vehicle speed sensor or odometer.

The operation of multiple imaging sensors can be synchronised such that they each trigger their data sampling at the same time. The raw data for different sensors at a common time/location can thus be cross-referenced within the indexed data store record.

For a predetermined distance of travel, e.g. as sensed by a predetermined number or fraction of wheel revolution on the tachometer, a pulse signal is output to the relevant image capture device to initiate an instance of image capture, e.g. as a frame/area, line or region scan. Therefore, if the train accelerates, the relevant sensor(s) will scan more quickly, and if the train decelerates, the scanning rate is lowered accordingly.

The wheel tachometer 24 provides a fixed number of pulse signals to the TrackVue connector/interface 26 (FIG.

3) for every wheel rotation thereby providing data on overall distance travelled, and speed of wheel rotation. The number of pulse signals is specified in terms of a fixed value per rotation. The wheel tachometer 24 pulse output rate is selected to work for a given maximum vehicle speed at a desired level of image resolution, e.g. such that the maximum scan rate is within the upper limit of the imaging sensors. TrackVue architecture is independent of the choice of the tachometer or speed sensor and can receive any suitable pulsed or other frequency control signal at interface 26. For example, both wheel tachos fixed to the wheel or portable versions using laser Doppler can work as they provide a trigger in a suitable format, such as transistor-transistor logic or low voltage differential signalling format.

Figure 3:
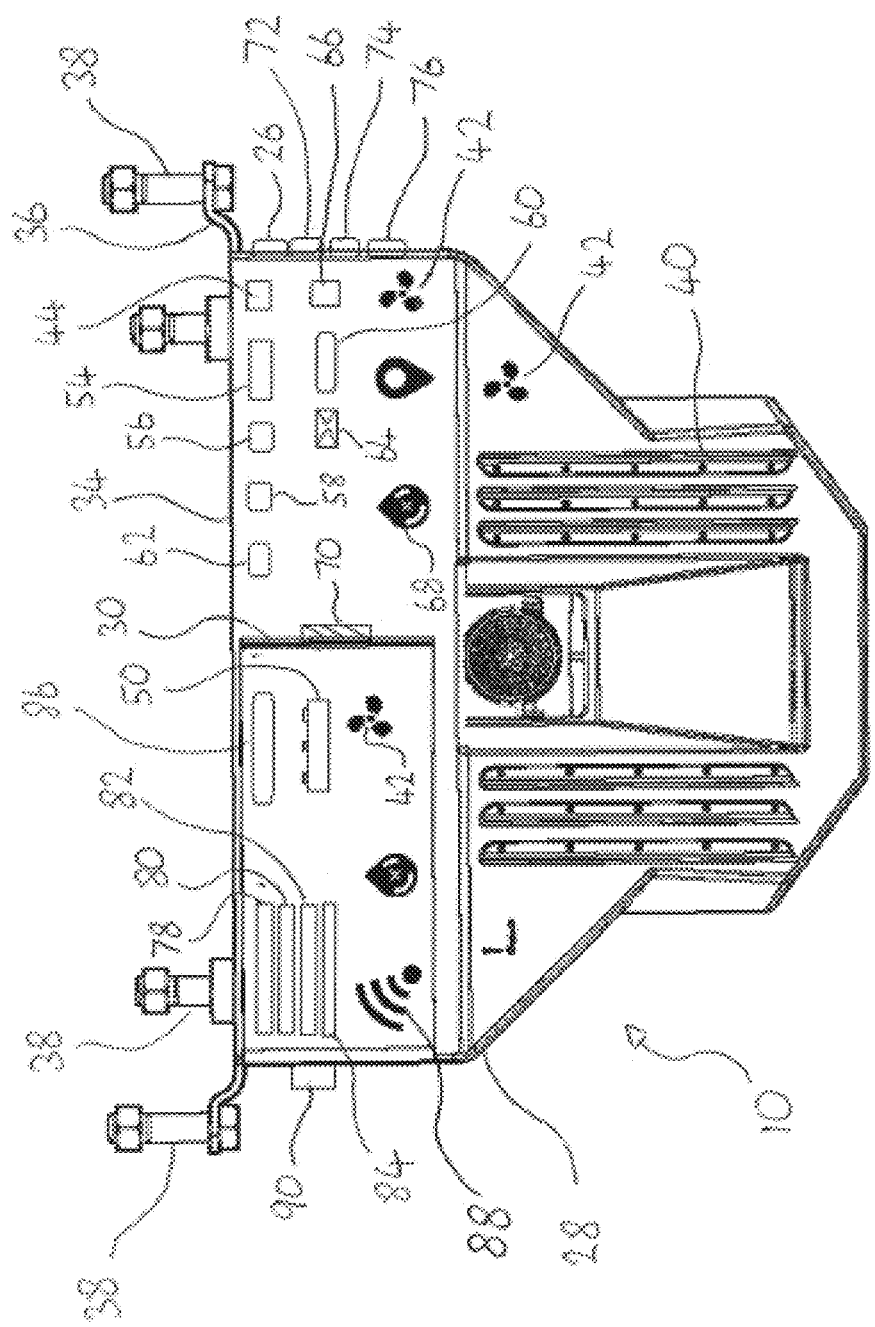
FIG. 3 shows a schematic layout of the components of the asset inspection system of FIG. 1 from above.

Turning now to FIGS. 2 and 3, there is shown an example of the image processing and ancillary equipment for operation of the asset surveying system. The overall system is broadly split into three separate compartments/modules that are provided together a single unit for installation on a train. These are: (a) The main housing 28 of the TrackVue enclosure that houses sensors, lighting and other ancillary components; (b) A removable processing unit (RPU) 30 that is mechanically and electrically coupled to/within the main housing 28 for use and consists of data processing, storage and control hardware; (c) A battery 32 that also integrates with the main housing 28 to allow for system operation in addition to the use of power supplied via the railroad vehicle.

The main housing 28 of TrackVue defines a hollow enclosure to which any of the aforementioned imaging equipment 11a, 11b, 11c, 14, 16 and any associated lighting 22 can be mounted. Corresponding openings/windows are provided in the housing 28 to allow imaging of the outdoor scene. The internal mounts within main housing enclosure may be adjustable, if needed, to allow for change in their viewing angles of the imaging sensors. Motorised/electrical angular adjustment mechanisms are preferably integrated into the camera/sensor mounts.

The main housing 28 has mounts for fixing the housing onto a railroad vehicle. In this example, a rear wall 34 of the housing 28 has mounting brackets 36 and fasteners 38, such as bolts, depending therefrom for attachment to a frontal portion, i.e. a leading wall, of a train. The front-facing nature of TrackVue 10 is beneficial to providing the required field of view for asset imaging. It may also be desirable to mount the TrackVue at a chosen height on the rail vehicle to mimic the driver's view of the track scene as far as possible.

The cooling of the interior of both the main housing 28 and also the RPU 30 is an important operational consideration for dissipation of heat generated by the imaging sensors, laser, LED lights, as well as any computational equipment. The exterior of TrackVue 10 will be air cooled by motion of the train in use and so conductive cooling of any heat sources can be accommodated by thermally coupling the heat sources to the external wall of the housing 28. Conductive fins 40 or other suitable structures on TrackVue exterior may beneficially increase the available surface area for heat loss to ambient air. Vents may be provided in the housing 28 to promote cooling air flow within the enclosure interior.

Appropriate cooling fans 42 can be provided within either or both of the main enclosure 28 and RPU 30 so as to promote convection cooling. If necessary, either or both of the main enclosure or RPU 30 could be provided with a liquid cooling system in the event that air cooling is insufficient alone to maintain the internal temperature at a desired level.

The main housing further comprises control/management circuitry 44 which monitors trigger/pulse signals, power supply, devices within TrackVue 10 and environmental readings. The management circuitry 44 is responsible for the operational state/health of the equipment and can output control signals to regulate their use so as to ensure equipment operation is maintained within desirable limits. The circuitry is responsible for managing a number of tasks including:

a) Monitoring and regulating internal temperature and humidity of TrackVue with its on-board temperature and humidity sensors. In case these parameters exceed their required threshold, the control circuitry can shut down the power to TrackVue or to individual devices therein. In such an event, an alert will be sent to a display 46 as shown in FIG. 5 of a monitoring console within the train 48 and/or to any other relevant communication/monitoring equipment through a Train Information Management System.

b) Monitoring the levels of battery charge and for charging it. This applies to the main battery 32 and/or a battery 50 internal to RPU 30. Any alerts of battery faults or insufficient charge may be reported by alerts as described above.

c) Modifying the incoming voltage power supply to suit the needs of imaging sensors and laser equipment and for redistributing it as needed.

d) Monitoring and modifying/improving the signal quality of the incoming trigger/pulse signal for controlling the rate of visual, thermal and/or laser image data acquisition.

e) Permitting and inhibiting camera and laser equipment operation such that those devices are only useable once the vehicle is in motion.

f) Providing an end-user with information on the health status of various TrackVue components through the LCD display 52 on TrackVue itself (FIG. 4), the monitoring console display 46 in the train cab and/or a remote console (FIG. 5). Rather than the asset survey data, this operational data concerns the system 10 health and may be used to understand operational issues, plan maintenance, etc.

g) Pulsing LED lights or lasers in order to reduce power consumption or reduce the heat generated by these.

The main housing 28 comprises an alert transmission unit 54 which transmits any alerts detected by either the control circuitry or by the processing equipment within the RPU 50, to a remote location either using wireless or wired connection. The alert may relate to the condition of the system, or an alert related to the track or detected assets.

In various embodiments of the invention, the main housing may comprise travel/environmental sensors, such as any, any combination, or all of:

A digital compass 56 providing direction of travel information;

An accelerometer and/or gyroscope sensor 58 to provide information on vehicle speed, acceleration, tilt and three dimensional position changes;

A vibration sensor 60 to monitor the level of vibration experienced by the unit;

A standard GPS or Differential GPS device 62 which records the latitude and longitude position of the vehicle at a set frequency In various embodiments of the invention, the main housing may comprise operational control devices, such as any, any combination, or all of:

A power supply unit 64 to convert the input current (e.g. at 24 VDC) to a 12 VDC or 5 VDC supply suitable for the system, e.g. including cameras and lasers (e.g. 12 VDC or 5 VDC);

A heating device 66 to warm up the entire unit to the minimum operational temperature in case the unit temperature drops below this minimal temperature threshold;

A dehumidifier unit 68 that is able to absorb the moisture from the air inside the unit.

The main housing has electrical/data connectors for communication of data signals and/or power such as any, any combination, or all of:

One or more connectors 70, such as internal and/or blindmate connectors, which allow for the RPU 30 to be mated with the main housing 28. The connectors 70 allow for transfer of data and power.

A number of external connectors including a connector 26 for supply of trigger signal from the wheel encoder or other suitable input;

a connector 72 for the taking power from the main power supply coming from the vehicle which has already been converted to 24 VDC or an appropriate voltage accepted by TrackVue;

a connector 74 for location data from an external device, e.g. RFID scanner or a third party location detection system aboard the train;

a connector 76 for high speed data transfer to a remote location through a wired connection, e.g. to the train data bus. This can be used where high volume real-time data needs to be transferred to an external storage on-board the vehicle. This may be required by the end-user to either carry out a more detailed, off-line data analysis, or to review all images collected from the track.

In its current format, the system allows for the use of battery power for short surveys because of limited capacity, and use mains power to charge it. As battery technology continues to develop, it is expected that longer surveys can be carried with battery power in the future. The current design allows for the battery 32 to be swapped easily from its own compartment in the field and replaced with a charged one to carry out recording. The battery charging and capacity status is displayed on the LCD display 52 and also relayed to the operator console 46.

The power delivered by the vehicle to TrackVue in its native state may not be 24 VDC and therefore a power converter 77 can be placed anywhere on the vehicle within a reasonable distance of TrackVue as shown in FIG. 5, if required, and should provide uninterrupted power at 24 VDC or a desired voltage level to the TrackVue. The on-board control circuitry 44 is able to further generate power at 5 VDC or 12 VDC for the cameras and laser devices from the 24 VDC input.

The image processor(s), software and data storage are housed within a separate RPU 30 housing. RPU 30 contains all computational equipment for data capture and processing. The RPU is purposely provided in a modular format such that it can be easily removed/replaced when required or taken off for offline data processing.

The RPU 30 thus comprises a self-contained unit which can process image data independently, provided it is supplied with the relevant incoming image data stream. For this reason, the RPU is provided within its own dedicated housing that is removable as a module from the main housing 28.

The RPU 30 comprises computer motherboard 78, high speed processor 80, Field Programmable Gate Array (FPGA) or frame grabber 82, graphics card 84, and a non-volatile data store 86, e.g. comprising one or more data disks, on which are provided one or more software module for processing captured visual, thermal and/or laser image data. The data store 86 also typically stores the image (i.e. pixel and or point coordinate data representing the captured images) and laser data itself, location data for each image and laser measurement, and/or any processed asset survey (i.e. asset classification and/or status) data.

An internal battery 50 for the RPU 30 is provided to ensure that, as a minimum, the internal processing components can be gracefully shut down if the unit is disconnected from the main housing battery or external power supply. Ideally the internal battery 50 would also allow continued data processing, i.e. for image processing jobs already commenced, even if disconnected from external power. The internal battery may also power a communications module for transmission of any relevant messages/data prior to shut down.

The RPU 30 has its own communication module 88, typically comprising and a conventional wireless transceiver. The module may allow communications to the vehicle operator in an attended mode of operation, or otherwise to an Operational Command Centre (OCC) in unattended mode. In both cases, the data related to analysis or alerts can also be sent by this unit to the Train Information Management System (TIMS). In addition, a 3G/4G wireless data connection device allows external access to TrackVue. The wireless connection can also be used for remote access to perform diagnostics, software updates, and repairs of the unit. Diagnostics on RPU can be further performed by attaching an external computer device through a physical external connector 90 which allows remote access to its components including computers and control circuitry.

To allow self-sufficient operation, the RPU 30 may also comprise one or more fan 42 for cooling the unit and/or dehumidification device 68 for absorbing unwanted moisture in the internal compartment.

Figure 11:
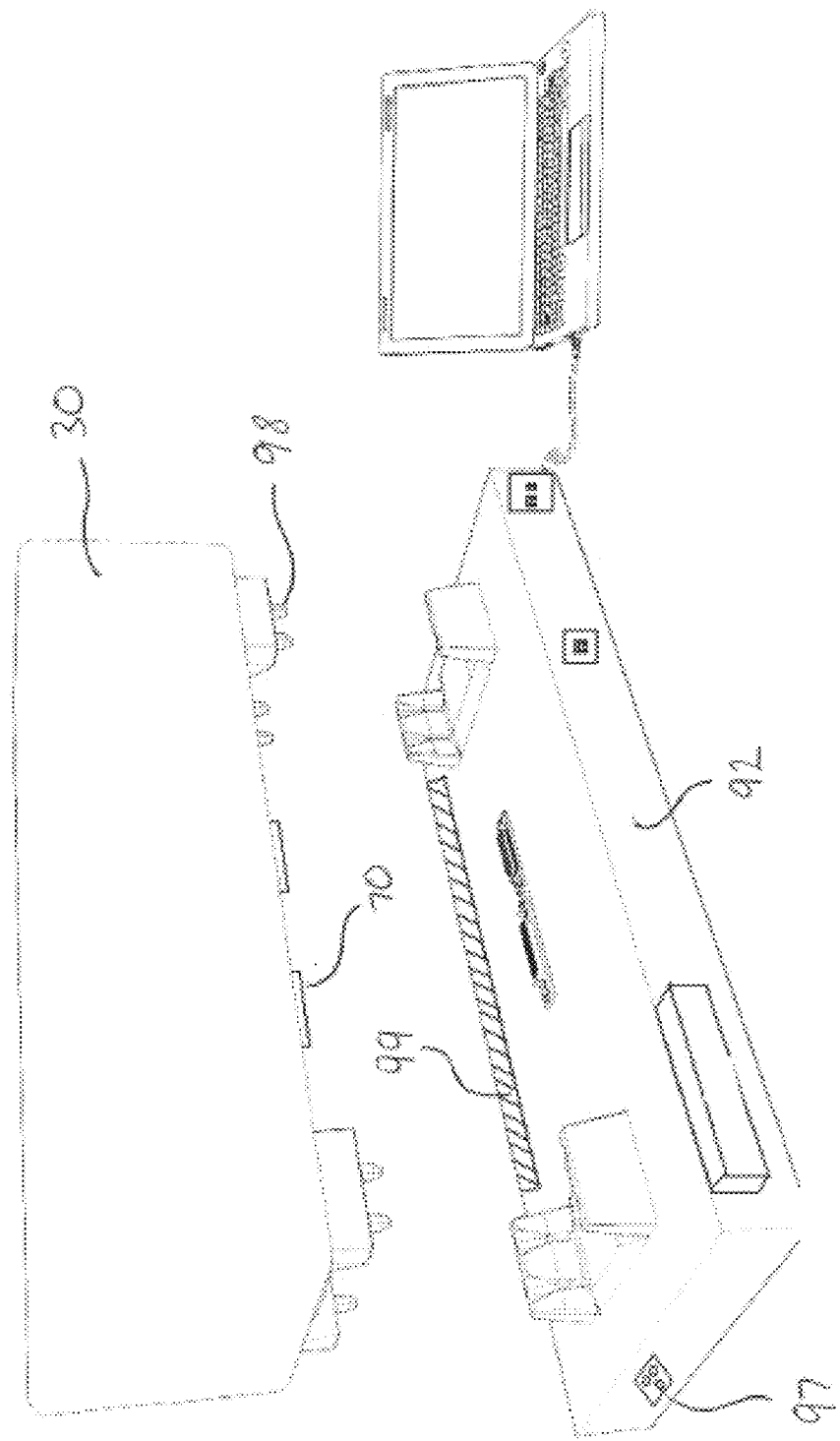
FIG. 11 shows an example of a removable data storage and/or processing device for use in conjunction with examples of the invention.

The RPU uses blindmate connectors 70 to attach to the main housing 28 of TrackVue body. This allows the RPU to be detached from the TrackVue as required by the operator and can be taken to a back an office environment for data processing using a docking station 92 as shown in FIG. 11.

The RPU allows two forms of data processing. Firstly, real-time data analysis which uses a combination of either high speed processor 80 coupled with FPGA 82 and/or graphics card 84 to process image/pixel data and/or numerical/point data generated by the laser imaging device. In such analysis, logged imaging results are instant and there is no growing queue of data to process in a buffer. The FPGA and processor are selected to handle the expected volume and speed of incoming data. Secondly, near real-time data analysis is possible using a library of software for high speed processor and graphics cards. Under these circumstances, the analysis is quick but not real-time and a buffer of unprocessed sensor data builds up over time. Near real-time analysis can be continued after all data acquisition has finished by either keeping the RPU attached to the main TrackVue body on the vehicle 73 as in FIG. 3, or by detaching it and later attaching it to its docking station 92 at a separate location, e.g. back office. Additionally, the data connections of the RPU 30 or main housing 28 could be used to offload logged image data in a format suitable for subsequent processing.

Figure 4:
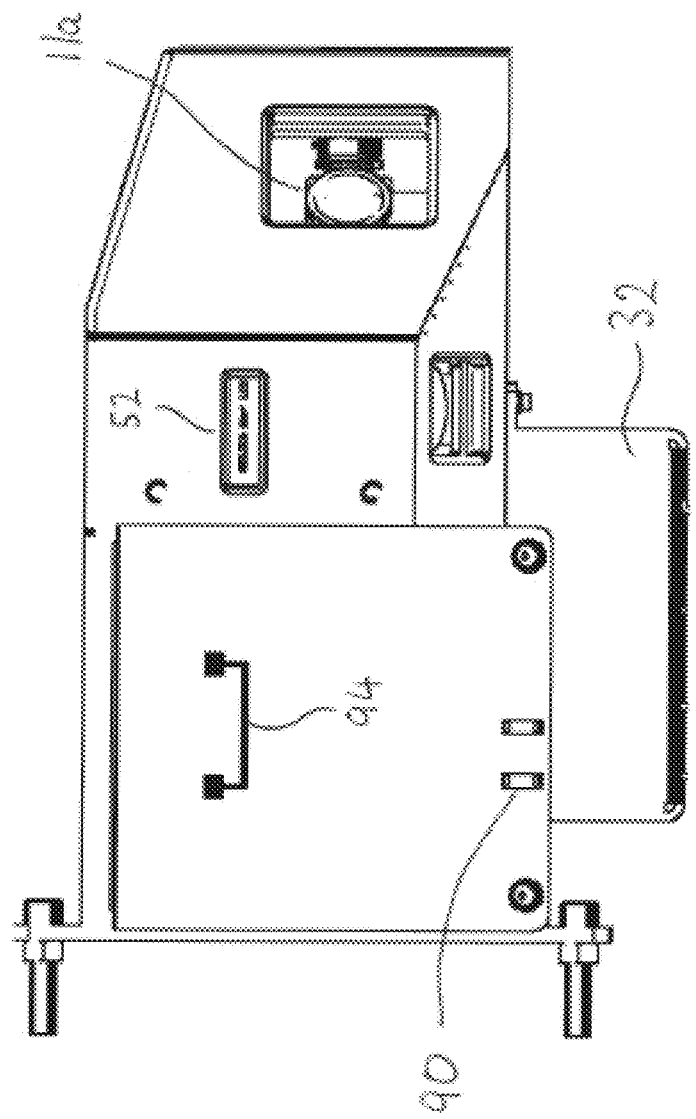
FIG. 4 shows a side view of the asset inspection system of FIG. 1.

FIG. 4 shows that the RPU 30 can be detached by pulling it out using a handle 94. The RPU itself forms a completely sealed assembly for outdoor use. Status related to RPU 30 or messages from control circuitry can be displayed directly on a touch panel display 52 which is visible to a human operator on the track when inspecting the system.

Figure 6:
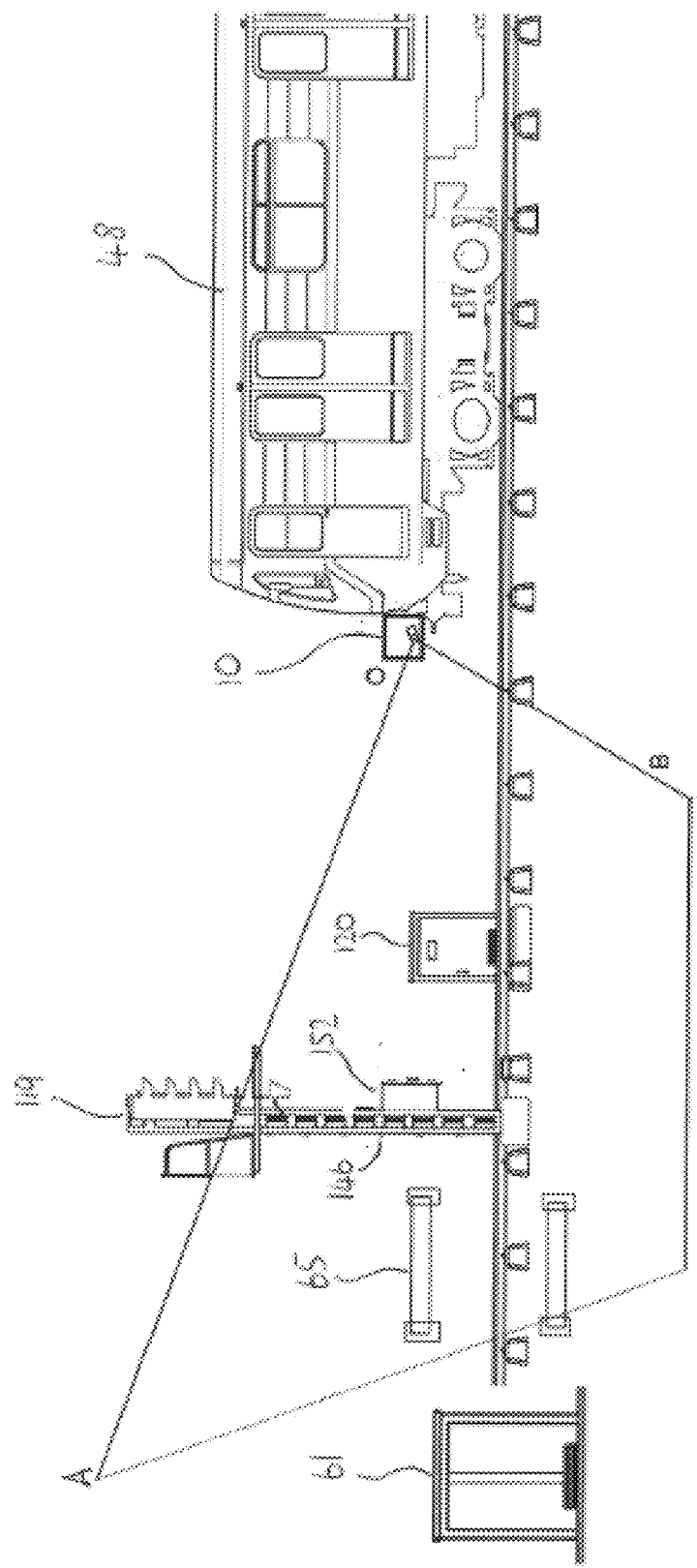
FIG. 6 shows a side view of an asset inspection system field of view according to an example the invention in use.
Figure 7:
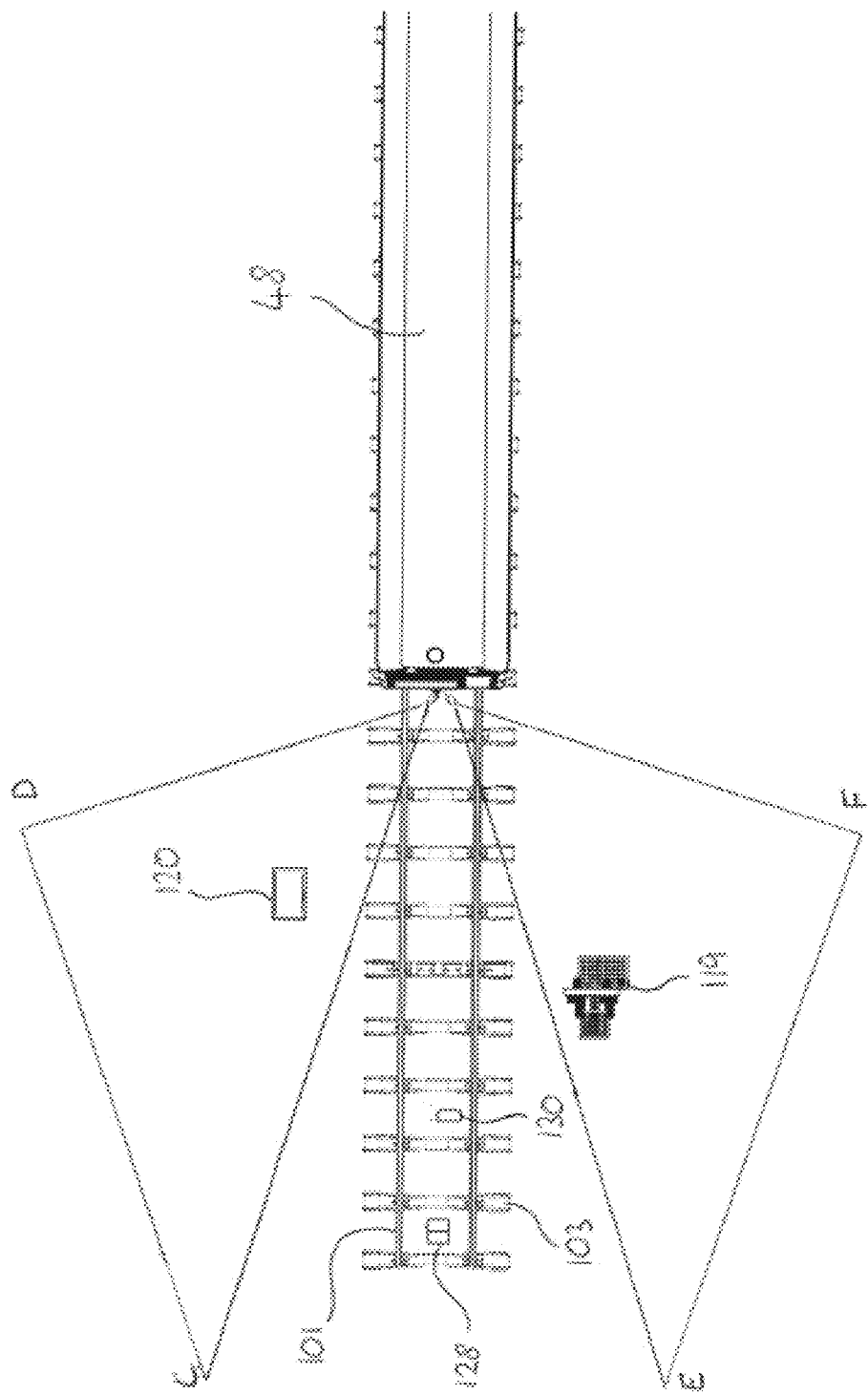
FIG. 7 shows an above view of an asset inspection system field of view according to an example the invention in use.
Figure 8:
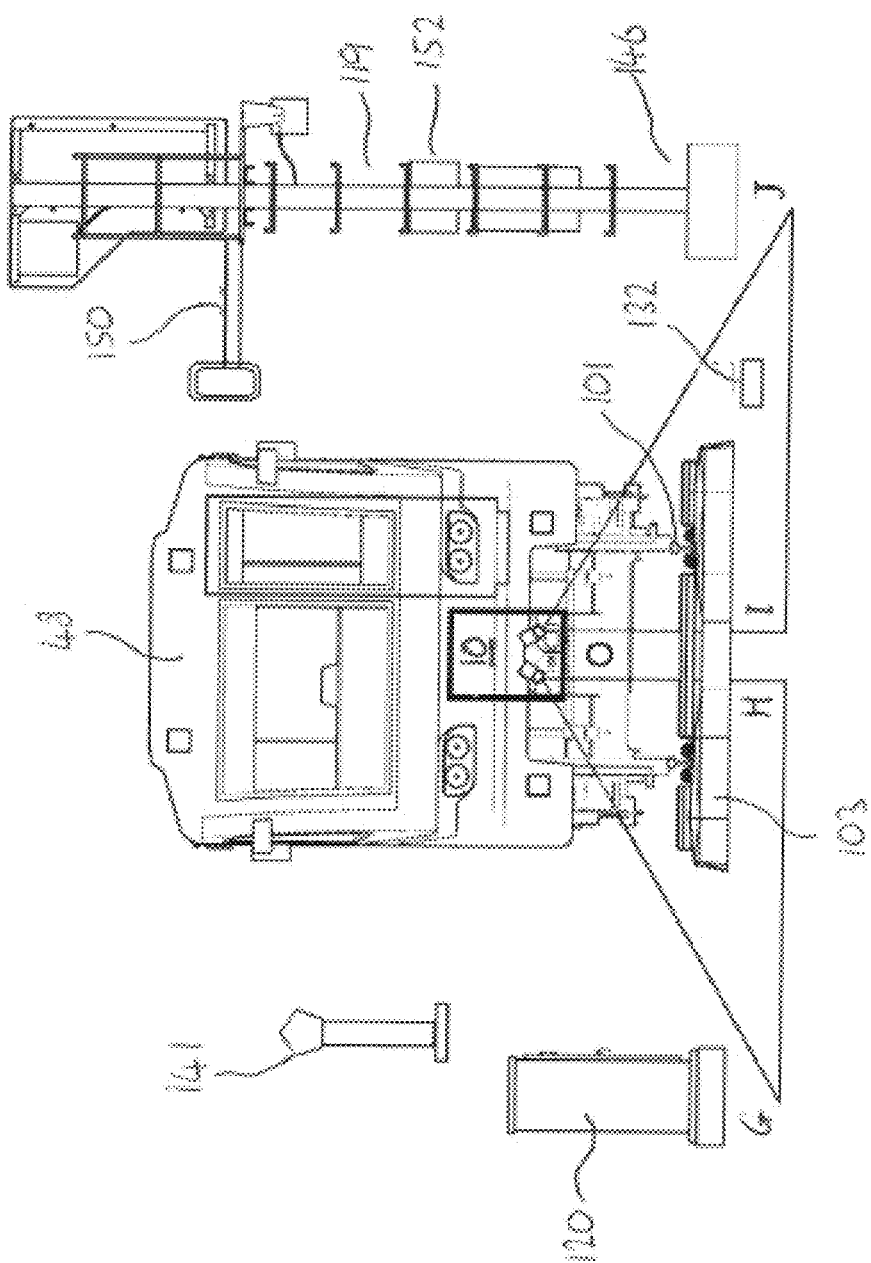
FIG. 8 shows a front view of an asset inspection system field of view according to an example the invention in use.
Figure 12:
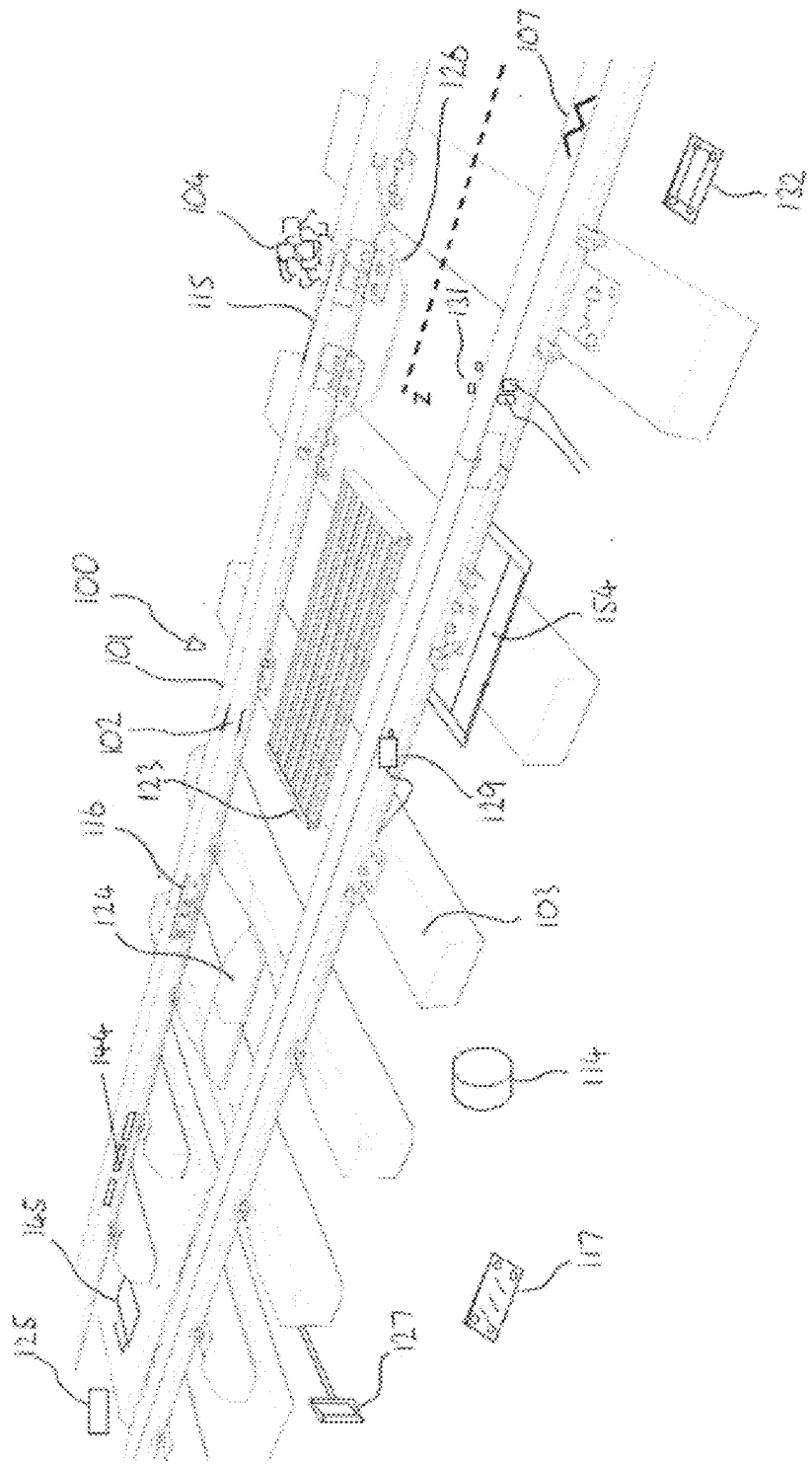
FIG. 12 shows examples of railtrack assets that may be inspected by examples of the invention.
Figure 13:
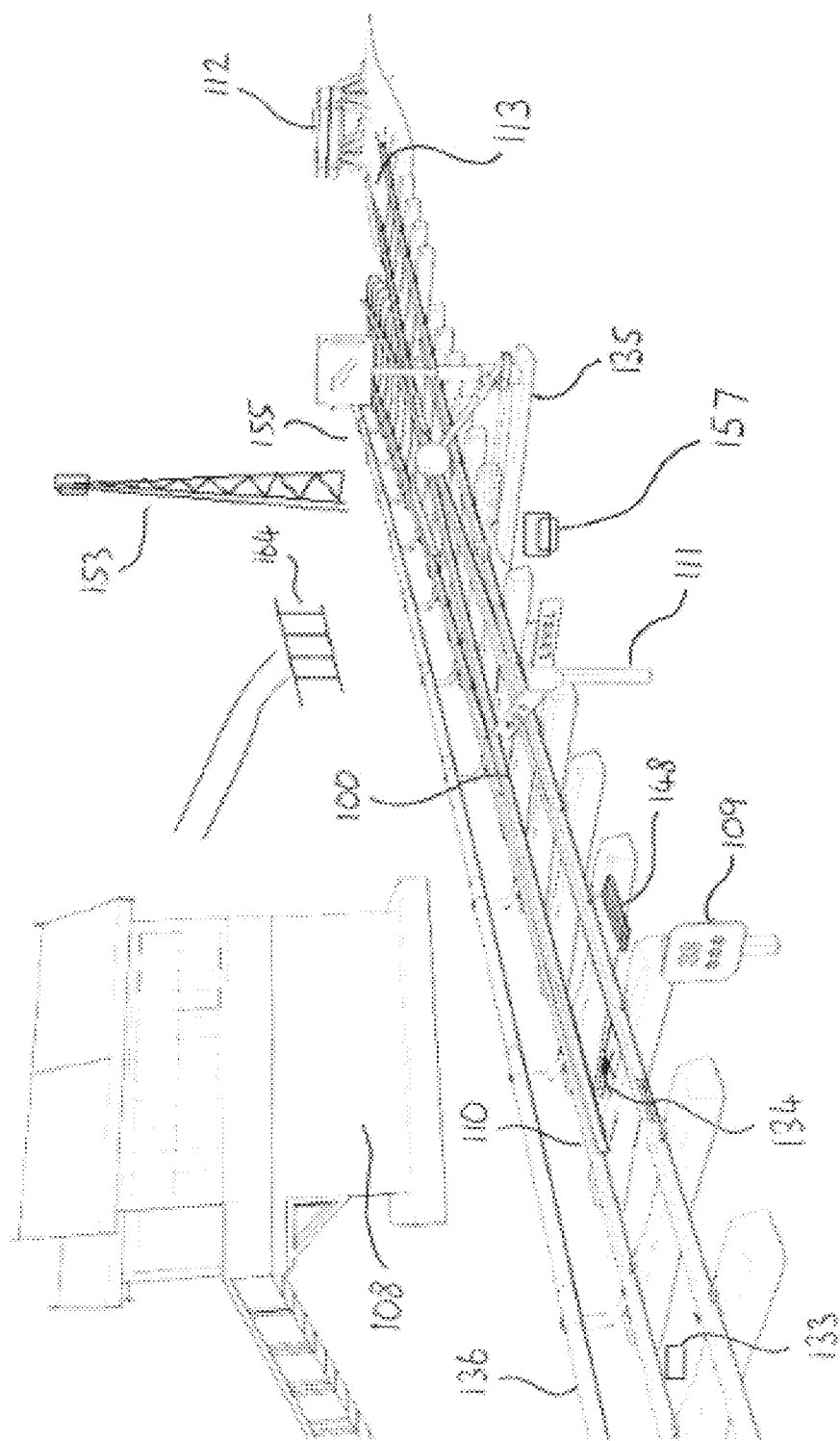
FIG. 13 shows further examples of track-related assets that may be inspected using a system according to the invention.
Figure 14:
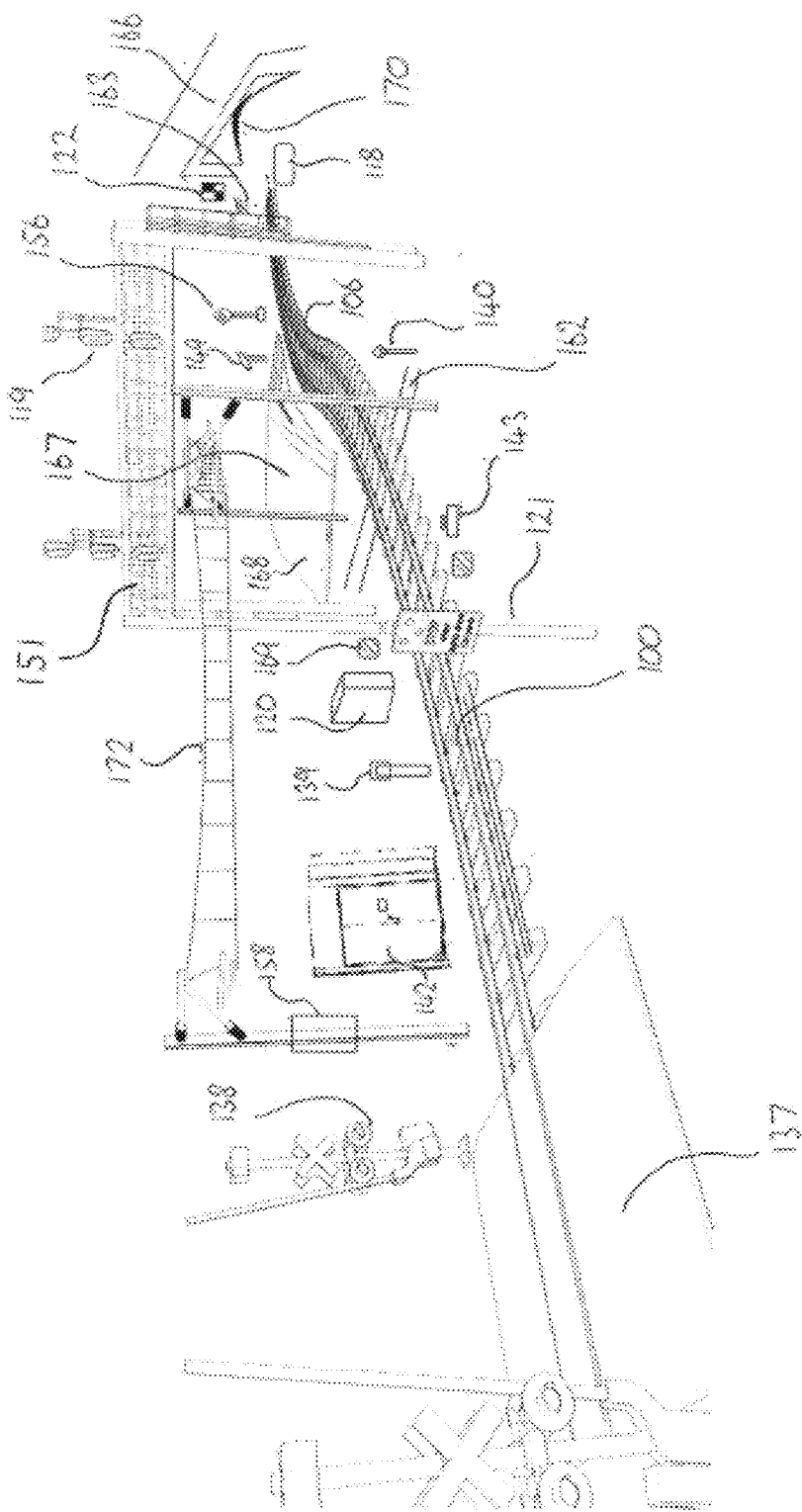
FIG. 14 shows further examples of track-related assets, including overhead assets that may be inspected using a system according to the invention.

FIG. 5 shows an example of mounting of TrackVue 10 to the frontal region of a passenger train 48, in a region immediately below a driver cab window 49. FIGS. 6 to 8 show the different fields of view of the different imaging sensors described in relation to TrackVue of FIGS. 1-4. FIGS. 12-14 show various examples of railroad-related assets that can be identified using the system, as referred to below FIG. 6 shows the field of view of centre imaging sensor 11b as the area visible within bounds OA and OB. The forward facing centre camera 11b is able to image in either colour or monochrome (grayscale) mode the following assets with a field of view centred on the track 100 itself (see FIG. 12): signals 119 (see FIG. 6); cantilever 150 (see FIG. 8), milepost 109, gradient post 111, buffer stop 112, ground frame 135, radio mast 153, electrification gap for third rail 155 (see FIG. 13), and curved track 106, driver signage (line speed, stop, etc.) 121, non-driver signage (trespass boards, grid power line clearance, etc.) 122, staff warning equipment 140, signal support gantry 151, traction signage 156, overbridges and tunnels 166, and cable bridge 170 (see FIG. 14).

FIG. 7 shows the field of view of imaging sensors as the area visible within bounds OC and OD on the right rail side and between bounds OE and OF on the left rail. The following assets are imaged in either colour or monochrome (grayscale) mode as desired with this field of view using areascan cameras and/or with thermal sensors where asset temperature is useful in their identification and recognition: electrical switchgear building 61, underbridges and viaducts 165 (see FIG. 6); signal or location cabinets 120, LED indicators 141, signal support 146, signal post telephone 152 (see FIG. 8); rail boundary 117, wheel impact load detector 144 (see FIG. 12); signal box 108, electrified rails 136, vehicle access points 164 (see FIG. 13); miscellaneous track equipment 118, level crossing floodlights 138, lockout device 139, equipment room 142, track to train transmitter 149, traction mounted auxiliary transformer or booster transformer 158, footpaths 162, foot access points 163, station platforms 167, station platform ramp 168 and under track crossings 169 (see FIG. 14).

FIG. 8 shows the field of view of these sensors looking downwards towards the track 100 within bounds OG and OH on the left side and OI and OJ on the right hand side. The following assets are detected in either colour or monochrome (grayscale) imaging mode as desired with this field of view using linescan cameras and/or with thermal sensors where asset temperature is useful in their identification and recognition: track circuit interference detector 130, impedance bonds 128 (see FIG. 7); rails 101 (see FIG. 8); rail side 102, sleepers 103, ballast 104, track centre line Z, stainless steel welded strip 107, track lubricator 114, expansion joint 115, insulated rail joints 116, TPWS TSS loops 123, balises 125, track circuit connections 126, track circuit tuning units 127, track circuit interrupter 129, axle counter head 131, hot axle box detector 132, wheel impact load detector 144, ATP beacon 145, automatic power control magnet 154 (see FIG. 12); point toe 110, sand drag 113, treadles 133, point mechanism 134, level crossings 137, tripcock tester 148 (see FIG. 13); miscellaneous signalling equipment (including airport trip wire, landfall detector, flood monitor, switch lock indicator, scotch block, depression bar, detonator placer, key release, close door (CD) switch) 143 (see FIG. 14).

Figure 9:
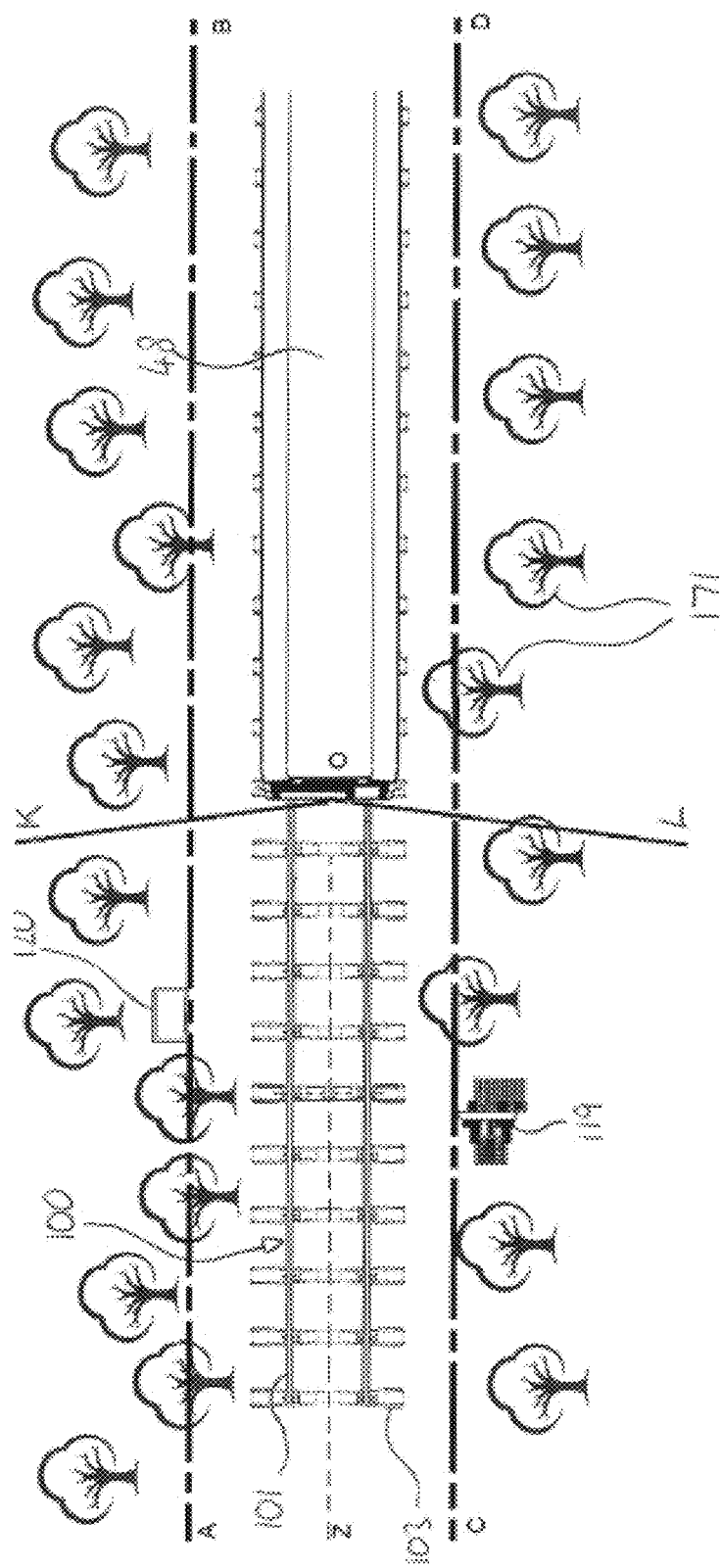
FIG. 9 shows an above view of an asset inspection system field of view according to an example of the invention.

FIG. 9 shows the field of view of overhead imaging sensor 20 as the area visible within bounds OK and OL. The following assets are imaged in either colour or monochrome (grayscale) mode as desired with this field of view: catenary wires 160 (see FIG. 5), vegetation 171 (see FIG. 9), and overhead electrical wires 172 (see FIG. 14).

FIG. 9 also shows the direction of motion of the train, i.e. the central axis Z of the track 100 and the centre of alignment for the imaging devices within TrackVue.

When an asset is imaged in more than one view, software for automated asset recognition may perform image analytics with both views to improve the overall asset recognition accuracy. In some cases, certain assets may be best recognised only in one view.

The laser imaging device 16 is also capable of profiling the track surface with a view to identifying track assets, such as, for example: track circuit interrupter 130 (see FIG. 7); point toe 110, sand drag 113, treadles 133, level crossings 137, tripcock tester 148, points heating transformer 157 (see FIG. 13); track lubricator 114, TPWS loops 123, automatic warning system magnets 124, balises 125, impedance bonds 128, axle counter head 131, hot axle box detector 132, wheel impact load detector 144, ATP beacon 145, automatic power control magnet 154, (see FIG. 12)

The scans generated by the laser unit can be further analysed independently on their own using one or two dimensional data analysis, or by first building a three dimensional surface and then applying three dimensional data analysis algorithms for determining the location of assets, and further estimating their identity based on dimension and shape measurements from such profiles. The profiles are subject to noise and without information typically associated with imaging sensors such as color and texture, the asset recognition software for analysing laser data alone achieves limited success. The asset identification and status assessment algorithms have been found to achieve better accuracy on asset recognition by combining laser sensor data analysis with imaging sensor data analysis wherever possible.

Figure 10:
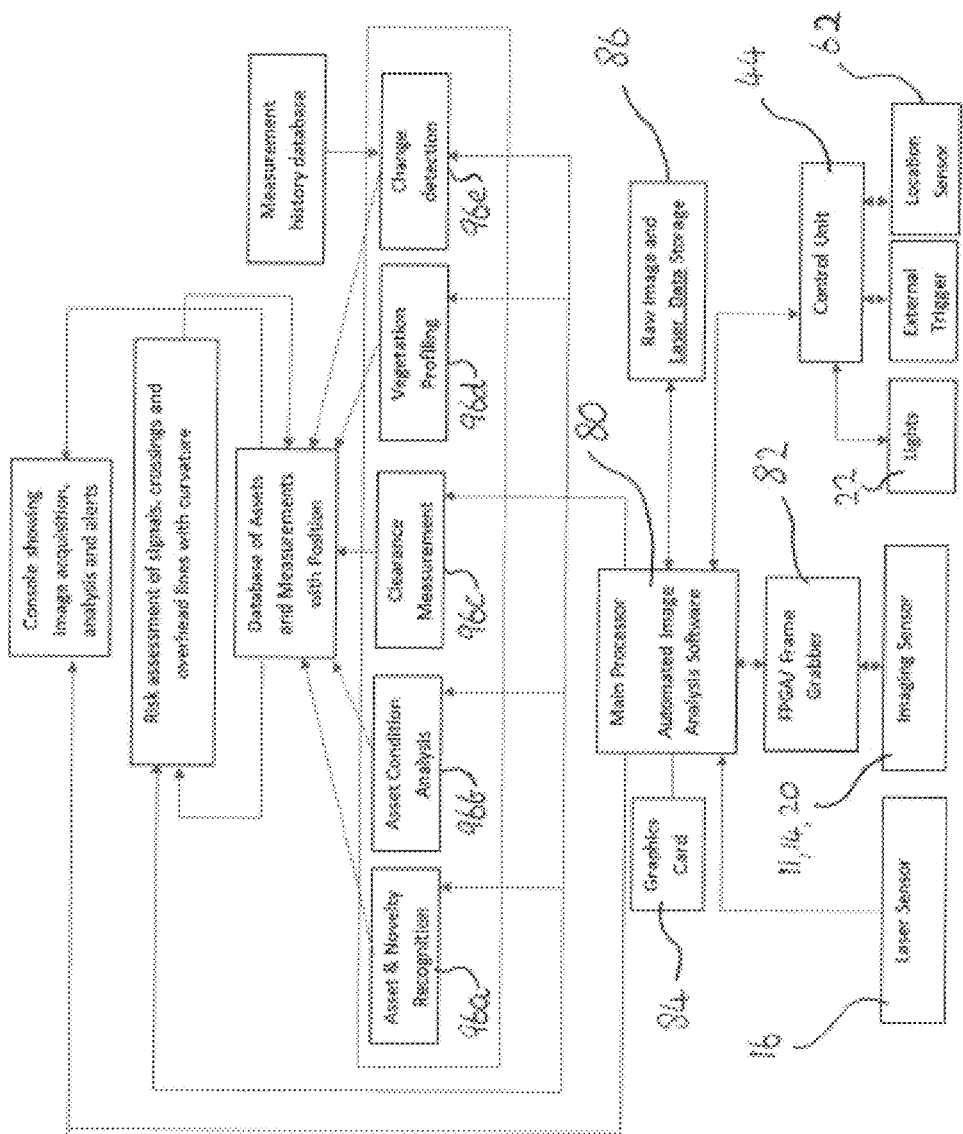
FIG. 10 shows a flow diagram of the image processing and asset surveying stages according to an example of the invention.

FIG. 10 details the overall data flow process from sensors to the alerts/reporting tools for the end-user, including the image processing stages to identify and analyse asset status. Any, any combination, or all of the process stages may be automated in accordance with examples of the invention. The above-described imaging sensors record data which is passed on to the main processor 80 on-board TrackVue. The imaging sensors' data output may connect directly to the main processor if no image compression is desired. If real-time compression is desired, e.g. to JPEG format, the data flows from imaging sensors to one or more FPGA or image grabbers, 82 which compress and reduce the quantity of data whist retaining the maximum possible image quality for further examination. The FPGA 82 also serves as the hardware used for real-time image analysis and would work together with the main processor 80 to load appropriate image analysis software for analysing image data. The number of input connections on an FPGA 82 may be limited and therefore if several imaging sensors need to be connected then more than one FPGA board may be needed.

The processor 80 can also use an array of graphics cards 84 to process data using near real-time data analysis, or simply store it in memory for analysis at a later time. The raw data is passed from the sensors to system memory for storage in parallel to sending it for processing. The main processor uses three major software modules.

A first software tool is for image and laser sensor data acquisition and controls the overall process of acquiring data including data flow from sensors, compression, sending it for analysis, recording it with a location (and optionally a timestamp) within system database, and storage on the physical hard disk 86.

A second software tool is for image and laser sensor data analysis and is responsible for executing a number of processing routines/algorithms on the collected data in either real or near real-time. If on-board data analysis option is not chosen, no data analysis is performed while data is collected. All data analysis in such cases is performed offline in a back office environment. For such cases, an FPGA can be replaced with a simpler frame grabber board which can only acquire data but cannot process it.

A third software tool manages a graphical user interface for the end-user that provides data review tools as well as performing general purpose database management to ensure that all data and its analysis is properly recorded with location and time information.

The main processor 80 decides which software algorithm must be used for which sensor data from a pool of algorithms available within the data store. The implementation of the software algorithms is different for different hardware, for example, whether they need to be executed on a graphics card or FPGA. All raw data needs to be stored to a physical memory 86 in addition to presenting it for analysis to appropriate processing hardware. For high speed data acquisition, storing JPEG images in real-time may be time consuming and therefore pixel data will be stored in a flat file structure which can be converted later into JPEG data by adding header information to it. Laser scans in compressed format are also stored in the non-volatile data store 86. The location for storage in terms of data directory can be specified by the system operator.

The system maintains a database record in the data store 86 that stores for each raw data image collected, its location including GPS latitude and longitude coordinates and a railroad line reference position. In cases where RFID location data is available, as discussed below, this will be stored in addition to, or instead of, other location data.

The image analysis software module portion of overall software suite is executed by the main, high speed processor 80, with or without the assistance of FPGA and graphics cards depending on the configuration. A software module or routine is a self-contained software tool which can take an image frame (typically in data format as a matrix of numbers) or laser data (as a one, two or three dimensional matrix of numbers), and apply a series of arithmetic operations 96a-96e as shown in FIG. 10 to process either the contents the incoming data represents, or to make measurements within such data.

As the first step of data analysis, an Asset and Novelty Detection tool 96a first identifies the contents of interest within an image. In case of two dimensional images, a matrix of numbers representing an image records for each position/pixel within the image, either a single value denoting the brightness of that pixel, or three numbers representing the red, green and blue channel color values for that pixel.

One or more arithmetic operation is used to cluster pixels of similar properties that are adjacent to each other, e.g. according to an image segmentation process. The image is thus broken down into a series of clusters by assigning pixels to clusters according to brightness/colour and proximity to other pixels of the same/similar properties. For each identified cluster, a series of further operations are applied that determine one or more property for the cluster, thereby defining a feature of the cluster that may be indicative of a corresponding feature of an asset captured in the image. The cluster properties assessed at this stage may comprise any or any combination of a cluster edge, colour, texture, shape and/or one or more other statistical property.

A general assumption is made that all pixels clustered together represent the same object/asset given their visual similarity. The identified properties of each cluster can be used by a classifier (e.g. a software tool that classifies or recognises the identity of objects in image data based on what it has been trained to recognise). Thus classification of each pixel cluster is used to classify the assets represented by the clusters.

Three separate types of classifiers are implemented within the system for asset recognition. Any or any combination of those classifiers may be selectively used as deemed suitable by the main processor 80. For example a classification confidence score may be assigned upon applying each classifier. Classifiers may be used sequentially, for example if the confidence score applied by use of one classifier is such that a further classifier is required to improve the certainty of asset/cluster classification. In this way the classifiers may be ordered in terms of computational efficiency or success rate, such that one classifier is attempted first followed by one or more further classifier. As an alternative to a pre-set classifier order, the processor may select a classifier according to an identified pixel property, e.g. dynamically.

The first type of classifier uses a set of rules to recognise the identity of an image object or image cluster which represents a real world rail track asset. A simple hypothetical rule can be: "If cluster object height is greater than 4 times its width at the bottom, AND object is less than 4 meters away from track centreline then it is a SIGNAL". Additional rules can be added to further refine the quality of recognition, e.g. "A SIGNAL must have an aspect with colour RED, GREEN or YELLOW". The key benefit of using a rule based classifier is that semantic rules from railways can be integrated with statistical rules to yield a high quality output. Additional rules can be added without affecting existing rules unless they contradict them, and there is no explicit training phase.

The second type of classifier used includes a template matching approach. For certain assets that have well defined shape and texture, they can be easily matched with a template. An asset template is a representative image of that asset that shows what it should appear as—i.e. a nominal asset image template. In the real-world, visual appearance of the same object will vary across images depending on their physical appearance and imaging conditions. Despite this, matching a pre-existing digital template of an asset type to a digital image of the same asset type provides a good way of identifying if the image contains that asset type and exactly where (in image coordinates) it does so. The system uses a range of correlation based matching methods as well as neural network and genetic algorithm based approaches to match pixel clusters to nominal asset templates. Again, a confidence score can be output according to the degree of correlation between the pixel cluster and the nominal asset template. A threshold absolute or relative confidence score may be used to assess if the match is sufficient to identify the asset type.

The third type of classifier used performs feature-based matching after training a classifier on known asset data. A table of training data is first generated from known images of assets. The table consists of N columns and M rows. The first N−1 rows consist of cluster attributes that have been extracted from segmented image clusters. An attribute can represent the edge, colour, texture, shape and other statistical properties of that cluster. The final column records the name of the asset. Each row of the table now represents data from a single cluster of pixels with the known identity of that cluster. Since this table is generated from images whose contents are known, it is known as training data. A variety of pattern recognition classifiers are used within the Track-Vue system to learn from such data including discriminant analysis and neural networks. Once trained, these classifiers are able to identify any known asset in a new image captured in real-time during system operation. Any data cluster which does not produce a good match with known objects is treated as a part of image background.

The identity of certain rail assets can be further confirmed through their identification with laser scan analysis of the track bed as well as the surrounding environment. These laser scans are processed to understand the shape of scan profiles according to the following process.

First, points of curvature change in laser profiles is measured which denote the edges of objects. The distance between two successive high curvature points is measured and evaluated for identity using a set of rules. For example, a raised segment with length close to 80 mm represents the railhead provided another such segment can be identified at further a distance equal to the gauge of the track. Thus in different aspects of the invention, whether using laser or camera imaging, proximity/distance between assets or asset features can be used to classify the asset as being of a predetermined asset type.

Second, template matching of scan segments is used to reveal their identity. Laser scan templates of known track objects can be matched against acquired data to determine whether or not a given asset exists within the laser profile. The template matching process can be performed with one dimensional depth information data or three dimensional point cloud data.

Furthermore, given that laser scans and 2D imaging data acquired in camera images, cross-referencing between features identified in those different types of data files can be undertaken based on corresponding time-stamps and or location data associated with the relevant feature. The depth-based information on asset sizes acquired from laser scans can be combined by two dimensional asset appearance measured in imaging sensors to improve on asset identification.

Finally, a three dimensional surface can be created from laser data which generates a point cloud (a series of scans combined together over time). Software can analyse clusters and patterns within this point cloud and measure object distances from track centreline to identify if they represent an asset of interest. If such an analysis is conducted independently on the laser data, its outcome can be combined with two dimensional image analysis of the same scene to accurately label assets on the track.

It will be appreciated that in using the above asset classification approaches, a plurality of asset attributes may be used in combination to improve classification accuracy. For example, classifying an asset according to a combination of color/texture and one or more geometric attribute, such as size, shape, edge profile, or the like can give greater confidence in asset type matching.

Once an asset is detected, the system logs in the data store 86 the asset type/label, the image identity (e.g. a sequence number) where the asset was found, a time stamp and location data of where the asset was imaged, e.g. relative to a known track location. This may represent a minimal data set to record and a working example of the invention may also log one or more of: asset properties within the image (information on its centroid coordinates within the image, dimensions horizontal and vertical, coordinates of points of interest or boundary pixels, color, edge and/or texture and/or shape data, etc.); position of the asset relative to track centreline and/or running rail (field side or gauge side); and confidence in detection, e.g. as a value on a confidence scale between 0 and 100, whereby 0 represents no confidence and 100 represents highest possible confidence. The confidence estimate is directly based on the level of match detected between the asset properties derived from one or more image and/or scan, and of those of known objects, and may additionally take into account the visibility of the object (i.e. according to whether the asset was partially obstructed and/or the quality of the lighting conditions).

Using the above techniques for asset classification, the asset recognition tool 96*a* may also serve as a novelty/anomaly detector. In the event that assets or objects are detected using the available sensor data that do not match any predetermined asset models/types (e.g. that do not meet minimum threshold confidence levels), the tool 96*a* can output a finding of an unclassified object. The images in which the anomaly is present may be logged and an alert output identifying the presence of an anomaly, e.g. including its location. Manual input may be required to identify the asset type, if necessary to update the record.

Once an asset has been identified by tool 96*a*, an Asset Condition Analysis tool 96*b* is applied to assess the condition of the asset. The tool 96*b* may comprise a plurality of software modules. In general, the tool 96*b* will compare the amassed image data for the identified asset against a predetermined (i.e. a nominal or previously recorded) asset model. The precise details of the model and/or the comparison undertaken will typically differ between different asset types. In certain respects this may be similar to the template matching process described above, except that now that the asset type is known, the differences between the imaged asset and the predetermined model can be extracted and/or quantified to provide an account of the asset status.

A comparison may be made between geometric attributes of the asset, for example such as the asset orientation, e.g. angular orientation or relative position, or one or more asset dimension. Comparison may be made additionally or alternatively between surface properties (texture, colour) of the predetermined and measured asset.

The surface condition of an asset can be analysed for detecting: (a) Wear and tear of the asset; (b) External markings such as graffiti; (c) Broken or missing components; (d) Change in orientation indicating damage; (d) Missing assets if prior information is available on what assets are expected on a given portion of track; and (e) Assets obstructed from view because of snow, mud or sand thereon. Imaging sensors can evaluate asset condition based on its visual appearance, change in colour, presence of edges which can represent cracks, change in object boundary orientation and so on.

Thermal sensors can pick up defective assets, for example broken cables, where the expected heat signature is affected. Laser scans provide valuable depth information which can represent certain defects on assets. Such analysis must be conducted once the asset has been reliably identified. A sudden change in depth profile of an asset may be normal for some, and abnormal in other cases. For example, a change in depth profile of a signal is fairly normal, whereas, one does not expect the same on a railhead where it should be flagged as a defect.

One aspect of asset recognition and/or condition analysis comprises asset visibility. Once an asset has been identified by the system in the captured image data, the either process 96a or 96c can determine the image in which the asset first became visible from the stream of logged images. By comparing the location of the image in which the asset is recognisable with the location of the asset, the system can output a visibility distance for the asset. The visibility distance may be logged for the asset. In the event that asset visibility distance is below a threshold acceptance value, an alert or log may be created accordingly. Thus any obstructions to asset visibility may be readily identified and rectified as necessary.

Asset condition analysis tool 96b may be seen as offering one type of asset status assessment. FIG. 10 shows further tools 96c, 96d and 96e for various other asset status assessments.

The Clearance Measurement tool 96c assesses the operational risk posed by an asset to the railroad by its proximity to the track 100. All tracks need to observe a fixed structural gauge which defines the size of rolling stock that can operate on the track, and go through bridges and tunnels. TrackVue image and laser data analytics recognise the presence of a known or unknown object close to the track which infringe the clearance envelope. The location and/or timestamp where the clearance envelope is infringed is recorded.

Within the above-described processes, it will be appreciated that rail track itself will be captured by the various imaging sensors and, as such, can be processed as being an asset. The presence of the rails at a defined gauge and spaced sleepers may be used to classify the track. Thus a central axis for the track maybe defined as lying midway between the rails and certain track attributes may be determined, such as the track curvature/orientation and/or any anomalies in the track, from visual and/or laser imaging of the track. An overhead cable may also identified as an asset associated with the track or track axis. The proximity of assets to the track and/or overhead cables may be determined and logged as an aspect of asset condition or associated risk.

The location data for assets may be determined from one or more suitable location sensor of the system. The location sensor 62 (FIG. 3) is a GPS sensor providing an output in terms of latitude and longitude coordinates. This may be useful in constructing a map/plan of the detected assets. However the location of assets may additionally or alternatively be defined in relation to a distance along the track and a spacing from the track, i.e. in terms of a coordinate/positioning system relative to the track. One method of locating position relative to the track comprises use of tachometer 24 (FIG. 5) to determine distance travelled along the track according to the number of wheel revolutions. Other travel distance sensors could involve RFID sensors, for detecting RFID tags located at known positions along the track. Location determination using a plurality of sensor types could be used to improve the certainty with which the TrackVue location, and hence asset locations, can be determined.

Vegetation encroachment towards the track and overhead lines is also measured using forward facing and overhead facing imaging and laser sensor data analysis using the Vegetation Profiling tool 96d. Vegetation detection is based on colour, texture and edge properties of vegetation, as well as potentially its thermal properties. The contours of vegetation, its density inside of this contour, colour, height and size properties are measured. The overhead imaging sensors can accurately profile the position of overhead lines along with vegetation and measure the closeness of the two. If the proximity infringes the clearance envelope, an exceedance is reported. Downward facing cameras also image leaves and weeds which are recognised and reported.

Furthermore, growth profiling may be accommodated by the tool 96d, such that an expected change in the extent of vegetation due to growth and/or seasonal variation can be applied to determine whether vegetation may encroach on a clearance envelope in the near future.

The Change Detection tool 96e identifies the changes in track itself or other assets over a period of time. For this, historical data containing previous analysis and raw data is used. For each location on the track, or for each corresponding asset, image content from multiple runs, i.e. corresponding images taken at different times, is compared. Examples of change detection include: (a) Recognition of objects on track (assets of interest or otherwise) that were not previously present but now appear, and vice-versa. This could be a result of maintenance activities, or changes in environment; (b) Changes in visual appearance of asset objects, e.g. a broken barrier; and (c) Changes in the environment such as vegetation overgrowth.

The integration of semantic knowledge or domain knowledge about track layout has been found to be of significant importance within the artificially intelligent machine learning algorithms which form part of asset recognition and/or analysis tools. This helps eliminate false detections and analysis, and provides a better recognition rate on objects (assets or defects) of interest. A comparison of successive runs can also assist with removing false positives.

Whilst the above system is described in terms of on-board processing steps, the real-time image data logging allows subsequent analysis of the captured data for asset recognition and status assessment. FIG. 11 shows a user console or system by which imaging data stored by the RPU 30 (FIG. 3) can be analysed at a later time (offline processing) after data capture. For offline processing, the RPU 30 can be detached and used within a back office environment. It requires a docking station 92 within such an environment to receive power for continuing data analysis operations. The docking station 92 takes power from a mains supply via a suitable power connector 97 and converts it to power that can be used by the RPU 30 by using a suitable power converter. Correct docking is assisted through the use of guiding pins 98 which align into corresponding docking formations in the station 92 for a secure mechanical and electrical connection. The power/data connectors 70 of the RPU 30 are received by corresponding connectors in the docking station 92. In order to keep the RPU and the docking station cool for extended periods of operation involved in any offline data analysis or review, a cooling unit 99 in the docking station 92 using either air/convention, conduction cooling or liquid cooling may be used. In order to use the data within the RPU for review and reporting, or for downloading or uploading files, the docking station can be connected to a computer which can access the RPU through it using a standard data connection, e.g. USB or Ethernet/RJ45 connector. The RPU can be connected to a local network for remote access through the relevant network connection.

In summary of the above description, TrackVue can offer a compact solution whereby all sensor and processing equipment may be packaged inside a singular rugged assembly. The solution is designed for easy attachment to a range of vehicles, especially passenger and inspection trains, and is significantly more compact than conventional track surveying and inspection systems that use separate in-cabin and out-cabin equipment. TrackVue is designed for low power consumption, which is a critical enabler for use on passenger trains, by reducing the number of electrical components used, improving system design, and by selecting low power yet high performance components. The external dependencies for operation of TrackVue are significantly reduced compared to existing inspection train systems and can use wireless communication with an operator console. The overall design therefore significantly reduces the cabling/installation burden as all connections between the camera and laser equipment, processing equipment and data storage are internal to TrackVue enclosure.

TrackVue can work in both "attended" and "unattended" mode. In the "attended" mode, the operator starts track surveying and inspection process by powering on the system through a console application which allows them to change any settings if needed before the start, otherwise, default settings apply. As track is surveyed, any alerts are fed back to the operator on their console through a desktop application which provides real-time display of images and statistics on what has been surveyed and inspected. For real-time image and laser data analysis, any assets detected are presented to the operator and can be overlaid on a map. In case of near real-time image/laser data analysis, a pool of image/laser data waiting to be processed is maintained and recorded in database. The position of the vehicle using one or more location sensors (e.g. GPS, line reference, RFID) is displayed for all assets and data collected. For laser scan based exceedance measurements, strip charts may display the measured value against pre-set thresholds. Thus two-dimensional or three-dimensional maps or plans of the surveyed route in which the track and identified assets are marked can be generated using the surveying system described herein.

At least one wireless or a wired connection is established between the system enclosure and a console mounted inside the vehicle for operator inspection and/or use. This transmits in real-time information on raw data, assets, their condition, measurements, and system status to the operator which can be displayed on the console.

A reporting tool allows for a range of asset survey reports and graphs to be generated. The format of reports and graphs is optimised for the end-user. Any problems associated with TrackVue performance or malfunction is displayed for correction at the operator console. At the end of vehicle run, the console also displays the current status of data analysis. If real-time analysis is chosen, all analysis is finished at the time of the end of the current run. In case of near real-time analysis, the console shows the amount of data waiting to be processed. At this stage, the operator has the option of continuing on with the analysis, or to stop the analysis. Any unfinished analysis can be carried out the next time TrackVue is started or by removal of the RPU and attachment to a power source, e.g. such as a docking station within a back office environment for completing all remaining data analysis. In this case the RPU serves as a replacement for data analysis in a back office environment. Once the data analysis is complete, the results can be offloaded from it through a USB connection by copying asset imagery and results database, or by simply removing a detachable disk.

A separate offline desktop software can be used by end-user in an office environment to perform a number of tasks including: (i) Reviewing of detected assets and their condition using rail route maps or other GIS maps where available, and applying tools for eliminating any false detections; (ii) Generation of survey reports for maintenance detailing assets and their condition; (iii) Comparison of analysis from multiple previous runs to see the changes in track condition; (iv) Generate clearance exceptions report detailing locations where the clearance envelope is breached; (v) Generate a risk assessment report for all signals, level crossings and overhead lines; (vi) Generate a 3D map of the track environment constructed from laser scans labelled for contents using information from 2D image analysis; (vii) Generate a report detailing novel features on track, for example excess sand, mud or snow, or unusual objects; (viii) Generate a vegetation profile report detailing vegetation density and types of vegetation (grass, shrub, tree); presence and density of leaves and weeds on the track from downward facing view is also reported; (ix) Print or export to portable devices various defect data, reports and any other statistics; (x) Plan maintenance for short or long term strategic planning on equipment repairs or replacement; (xi) Plan for any track renewals; (xii) Exporting analysis to a centralised Engineering Data Management System which contains a wider set of track condition information; (xiii) Exporting analysis to any web-portals or external databases; (xiv) Exporting analysis to portable devices which can be used by track engineers to walk the track; (xv) Comparison of automated data analysis reports with relevant track maintenance or track walking records to audit their quality; and (xvi) Review imaging sensor data analysis integrated with laser scan data. In this case, assets are first recognised in 2D image analysis, and a point cloud cluster generated from laser scans is evaluated to find the same asset in it. For a good match, the laser point cloud data cluster is labelled as the identified cluster.

Tools are provided to now navigate this labelled 3D data for understanding the three dimensional position of known assets, and making distance based measurements to understand the spatial relationship between assets and between track centreline and assets. The use of desktop software also allows further data to be imported from external sources to provide further context for data interpretation by a human operator.

During use on-board a railroad vehicle, in an "unattended mode", the system starts automatically on receiving power from the external source. Data acquisition sensors and lighting units are triggered to start operation once data from the wheel tacho or other suitable signal input confirms that the vehicle is in motion. If the vehicle stops for a period greater than a pre-set threshold, the sensors stop recording. The system does not require a console to display data acquisition or defect analysis. Instead, the results are transmitted to the Train Information Management System (TIMS) directly, or through email/wireless communication to an external Command Control Centre (CCC). Any further actions taken on such communication is the responsibility of TIMS or CCC. In case if a "near real-time" data analysis approach is employed on an unattended system, it is programmed to continue data processing as long as mains power or battery power is available and buffer data analysis for future runs if needed.

The developed system is designed to image and assess asset condition either on the ground level on a railway track as shown in FIG. 12, assets around the rail track and at differing heights above the ground level as shown in FIG. 13 and FIG. 14. For each asset, its distance in millimeters from the track centreline, its dimensions and position longitudinally along the track from a fixed point of reference can be noted. Furthermore, a GPS, RFID and/or line reference position is also recorded.

The system can be used for a wide variety of tasks including asset recognition and registration, asset condition monitoring, change detection, signal and level crossing sighting and risk assessment, vegetation profiling including risk evaluation for overhead lines, generating 2D and 3D maps of track with assets embedded within such a map, clearance measurement, detection of novel and threat objects, and measurement of track properties such as curvature. Thus the invention may allow plotting the analysis results with the available location data to produce Geographical Information System (GIS) maps for print or export. By repeating the analysis at regular time intervals, changes in component conditions and changes in level of risk related to signal visibility and vegetation encroachment of overhead lines can be detected.

The system can thus be used to generate risk reports on assets which will contain information on their identity, position, visibility, clearance status, and/or risk severity. Reports containing information obtained through use of the invention may be used for planning asset checks, maintenance, repair, removal and/or replacement.

What is claimed is:

1. A railroad track asset surveying system comprising:
a plurality of image capture sensors mounted on a railroad vehicle, wherein the image capture sensors comprise a plurality of sensor types of different sensor dimensionality;
a location determining system for images captured by the sensors; and
an image processor comprising:
an asset classifier for detecting an asset in one or more captured image and classifying the detected asset by assigning an asset type to the detected asset from a predetermined list of asset types according to one or more feature in the captured image; and
an asset status analyser for identifying an asset status characteristic and comparing the identified status characteristic to a predetermined asset characteristic so as to evaluate a deviation therefrom;
wherein the image processor automatically cross references images captured by the plurality of different types of image capture sensors.

2. The system according to claim 1, wherein the predetermined asset status characteristic comprises a nominal asset status characteristic and/or a previously detected asset status characteristic.

3. The system according to claim 1, wherein the image capture sensors comprise a shape and/or surface property sensor.

4. The system according to claim 3, wherein the plurality of image capture sensor types comprise any combination, or all, of: an areascan imaging sensor, a linescan imaging sensor, a three-dimensional surface profile sensor and an asset distance sensor.

5. The system according to claim 4, wherein at least one of the three-dimensional surface profile sensor and the asset distance sensor comprises a laser sensor device.

6. The system according to claim 3, wherein the image capture sensors comprise a light sensor for sensing brightness and/or colour within a visible wavelength band.

7. The system according to claim 6, wherein the plurality of image capture sensor types comprise any combination, or all, of an areascan imaging sensor, a linescan imaging sensor, a three-dimensional surface profile sensor and an asset distance sensor.

8. The system according to claim 7, wherein at least one of the three-dimensional surface profile sensor and the asset distance sensor comprises a laser sensor device.

9. The system according to claim 3, wherein the system comprises a thermal imaging sensor.

10. The system according to claim 1, wherein the plurality of image capture sensors are used and at least one of the asset classifier and asset status analyser correlates an asset feature in an image captured by one sensor with a corresponding image captured by one or more further sensor.

11. The system according to claim 1, comprising:
each of the plurality of image capture sensors being mounted in a different angular alignment so as to have a different field of view relative to the direction of travel of the rail road vehicle;
wherein each image capture sensor faces in a different one of a forward, downward, upward or lateral direction relative to the direction of travel and the image processor automatically processes said different fields of view for a common location.

12. The system according to claim 1, wherein the asset feature comprises an edge profile and/or dimension of the asset, and geometric features or template matching is used to determine a degree of similarity between the feature of the detected asset and a predetermined geometric feature or template.

13. The system according to claim 12, wherein a confidence score is determined and assigned to an asset classification or status analysis by the system according to a degree of the match between the detected asset feature and the predetermined feature or template.

14. The system according to claim 1, wherein the asset feature comprises a surface property profile of the asset and surface property feature or template matching is used to determine a degree of similarity between the feature of the detected asset and a predetermined surface property feature or template.

15. The system according to claim 14, wherein a confidence score is determined and assigned to an asset classification or status analysis by the system according to a degree of the match between the detected asset feature and the predetermined feature or template.

16. The system according to claim 1, wherein the system outputs an indication of anomaly detection in the event that the degree of similarity between the detected asset and the predetermined template is below a threshold level for positive asset classification.

17. The system according to claim 1, comprising a plurality of asset classifiers comprising two or more of a rule-based classifier, a template-based classifier and a statistical feature matching tool.

18. The system according to claim 1, wherein the image processor identifies one or more pixel cluster within an image according to one or more pixel brightness or colour property, each pixel clusters being used by the asset classifier and/or asset status analyser used to determine an edge, colour, texture or shape feature of an asset.

19. The system according to claim 1, wherein the asset status analyser determines the spacing between an asset and the railroad track and compares the determined spacing with a predetermined threshold minimum clearance and outputs the asset status characteristic in dependence thereon.

20. The system according to claim 1, wherein the predetermined asset status comprises a previously determined asset status characteristic, and the asset status analyser determines a change in asset orientation, shape, edge and/or colour relative to the previously determined asset status characteristic.

21. The system according to claim 1, wherein the asset status analyser analyses a plurality of asset status characteristics and outputs an asset status indicator comprising an aggregate of said asset status characteristic analyses as a single value on an asset status severity scale.

22. The system according to claim 1, wherein the image processor comprises a plurality of automated data processors, wherein a first processor is arranged to collate and log captured images and associated location data in real time in a data store, and at least one further processor may be arranged to process the captured images in parallel with the first processor to classify and/or analyse asset status, wherein the data store may comprise a buffer portion for amassing images to be processed by the at least one further processor.

23. The system according to claim 1, wherein the image processor comprises a central processor and either or both of a field programmable gate array and a graphics card for performing a function of the asset classifier and/or asset status analyser.

24. The system according to claim 1, wherein the location determining system comprises a vehicle travel distance sensor and/or a track position sensor, the location determining system outputting a location indication as a one-dimensional measure of distance along the track from a fixed track reference point.

25. The system according to claim 1, wherein the rate of image capture is controlled automatically according to the railroad vehicle travel speed.

26. The system according to claim 1, wherein the operation of the image processor including at least one of the asset classifier and the asset status analyser is automated upon receipt of captured image data and/or location determination data.

27. The system according to claim 26, wherein the asset classifier and asset status analyser perform automated image analytics by use of software modules for processing image data to generate one or more output comprising the identity, properties and condition of each identified asset.

28. The system according to claim 27, wherein asset and condition information, including defect data with location information, is transmitted wirelessly from the railroad vehicle to a central control or data centre from where end-users can retrieve it for further analysis and maintenance planning.

29. The system according to claim 1, wherein the image processor cross references images captured by the plurality of different types of image capture sensor according to a corresponding time stamp and/or location determination between said images.

30. The system according to claim 29, comprising at least one two dimensional image capture sensor and a laser sensor for capturing a three dimensional image in the form of an asset surface profile, wherein the asset classifier and/or asset status analyser automatically integrates said different sensor inputs for a common location determination.

31. The system according to claim 1, further comprising: a transmitter arranged to transmit a visual output signal to an operator console, the visual output signal having at least one of a combination of 2D or 3D maps indicating identified assets, asset risk reports, and/or asset data graphs suitable for maintenance purposes.

32. The system according to claim 1, further comprising: a local data store, wherein captured images from the image capture sensor and location data from the location determining system are indexed by the image processor within one or more database in the local data store.

33. The system according to claim 1, wherein the asset classifier comprises a vegetation classifier and the asset status analyser comprises a vegetation status analyser.

34. The system according to claim 1, wherein the asset status analyser outputs risk assessment data for railroad track assets comprising signalling, level crossings and overhead lines.

35. The system according to claim 1, wherein the image capture sensors, the image processor and location determining system are configured for mounting to a passenger and freight railway vehicle or locomotive in use.

36. The system according to claim 1, wherein the image capture sensors, the image processor and location determining system are provided as a singular assembly, said assembly further comprising at least one of the following:
 a battery for operation of the system in isolation of external power and;
 a removable processing unit configured to allow the image processing unit and an associated data store to be removed from the remainder of the system in a modular fashion.

37. The system according to claim 1, being arranged to operate selectively in both an attended mode in which a human operator provides control inputs for image data acquisition or control of the asset status analyser, wherein operator software tools are available for review and reporting of asset status information, and an unattended mode, wherein the system operates fully autonomously according to a preprogrammed set of machine readable instructions embedded within it.

38. The system according to claim 37, wherein the unattended modes do not require human intervention for starting, stopping, data acquisition or analysis and is fully automated from data collection to transmission of data analysis to an operational control centre.

39. The system according to claim 1, wherein the assets comprise the railroad track, railroad track-mounted assets and objects in the vicinity of the railroad track.

40. A railroad track asset surveying method comprising:
 operating a plurality of image capture sensors mounted on a railroad vehicle during motion of the railroad vehicle along a track, wherein the image capture sensors comprise a plurality of sensor types of different sensor dimensionality;
 determining and logging a location of the image capture sensors for each image captured by the sensors, and
 automatically processing the captured images upon receipt using one or more computer processor by detecting an asset in one or more captured image and classifying the detected asset by assigning an asset type to the detected asset from a predetermined list of asset types according to one or more feature identified in the captured image, and identifying an asset status characteristic and comparing the identified status characteristic to a predetermined asset characteristic so as to evaluate a deviation therefrom.

41. A physical storage medium comprising machine readable instructions for the operation of a railroad track asset survey image processor configured to:

receive images captured by a plurality of image capture sensors of different dimensionality mounted on a railroad vehicle during motion of the railroad vehicle along a track;

log a geographic location for each image captured by the sensor;

process the captured images by detecting an asset in one or more captured image and classifying the detected asset by assigning an asset type to the detected asset from a predetermined list of asset types according to one or more feature identified in the captured image; and identify an asset status characteristic and comparing the identified status characteristic to a predetermined asset characteristic so as to evaluate a deviation therefrom, and output an asset status indication based upon said deviation.

42. The physical storage medium according to claim 41, comprising individual modules responsible for: real-time data acquisition of said images and geographic locations; high speed data analysis comprising said classifying the detected asset identifying asset status characteristic; and, transfer of asset status indications to one or more external interfaces, wherein the high speed data analysis module is selectively useable and/or reprogrammable.

43. The physical storage medium according to claim 41, wherein the asset survey image processor is arranged under the control of the machine readable instructions to receive raw captured image data as input either directly from the image capture sensor, or after a plurality of individual images into one or more combined image, and to output automatically a determination on the presence or absence of a recognisable asset, an asset classification and the asset status indication comprising any or any combination of asset condition grade, an asset size, shape and/or colour property, and asset change relative to a previously recorded asset status indication.

44. The physical storage medium according to claim 41, wherein the image capture sensors comprise one or more of linescan, areascan and thermal imaging sensors mounted with a view of the rail track and the machine readable instructions for classifying the asset and/or outputting the asset status indication comprise a plurality of image analysis operators for any combination or all of edge detection, edge analysis, texture analysis, shape analysis, statistical analysis of pixel distribution data, colour analysis, image enhancement, image segmentation, template matching using statistical and neural network methods, feature based object recognition, rail track environment semantic knowledge analysis.

45. The physical storage medium according to claim 41, comprising instructions to store in a database an image location for the asset including an asset boundary, minimum and maximum image coordinates in horizontal and vertical directions, a centroid for the asset and one or more visual feature of the asset such as a colour or topology features.

46. A system according to claim 1, wherein the image processor automatically cross references images captured by the plurality of different types of image capture sensor according to a corresponding time stamp and/or location determination between said images.

47. A system according to claim 1, wherein the different types of image capture sensor each face in a direction of travel of the railway vehicle and generate two and three dimensional views of a scene comprising assets in the vicinity of the track.

* * * * *